US012404320B2

(12) United States Patent
Payton et al.

(10) Patent No.: US 12,404,320 B2
(45) Date of Patent: Sep. 2, 2025

(54) DOSAGE AND ADMINISTRATION OF ANTI-C5 ANTIBODIES FOR TREATMENT OF PAROXYSMAL NOCTURNAL HEMOGLOBINURIA (PNH) IN PEDIATRIC PATIENTS

(71) Applicant: Alexion Pharmaceuticals, Inc., Boston, MA (US)

(72) Inventors: Lori Payton, Madison, CT (US); Scott T. Rottinghaus, Salem, CT (US); Rajendra Pradhan, New Haven, CT (US); Stephan Ortiz, Wellesley, MA (US); Masayo Ogawa, Woodbridge, CT (US); Xiang Gao, Guilford, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 739 days.

(21) Appl. No.: 17/057,867

(22) PCT Filed: May 29, 2019

(86) PCT No.: PCT/US2019/034293
§ 371 (c)(1),
(2) Date: Nov. 23, 2020

(87) PCT Pub. No.: WO2019/231893
PCT Pub. Date: Dec. 5, 2019

(65) Prior Publication Data
US 2021/0214425 A1    Jul. 15, 2021

Related U.S. Application Data

(60) Provisional application No. 62/678,455, filed on May 31, 2018.

(51) Int. Cl.
C07K 16/18 (2006.01)
A61K 9/00 (2006.01)
A61P 7/00 (2006.01)
C07K 16/28 (2006.01)
A61K 39/00 (2006.01)

(52) U.S. Cl.
CPC ............ *C07K 16/18* (2013.01); *A61K 9/0019* (2013.01); *A61P 7/00* (2018.01); *C07K 16/283* (2013.01); *A61K 2039/505* (2013.01); *A61K 2039/54* (2013.01); *A61K 2039/545* (2013.01); *A61K 2039/55* (2013.01); *C07K 2317/24* (2013.01); *C07K 2317/52* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,710,795 A | 1/1973 | Higuchi et al. |
| 4,485,045 A | 11/1984 | Regen |
| 4,544,545 A | 10/1985 | Ryan et al. |
| 4,816,567 A | 3/1989 | Cabilly et al. |
| 4,863,457 A | 9/1989 | Lee |
| 4,868,116 A | 9/1989 | Morgan et al. |
| 4,980,286 A | 12/1990 | Morgan et al. |
| 5,013,556 A | 5/1991 | Woodle et al. |
| 5,308,341 A | 5/1994 | Chanoch |
| 5,443,505 A | 8/1995 | Wong et al. |
| 5,447,145 A | 9/1995 | Cappello et al. |
| 5,501,856 A | 3/1996 | Ohtori et al. |
| 5,624,821 A | 4/1997 | Winter et al. |
| 5,648,260 A | 7/1997 | Winter et al. |
| 5,773,019 A | 6/1998 | Ashton et al. |
| 5,997,848 A | 12/1999 | Patton et al. |
| 6,001,329 A | 12/1999 | Buchsbaum et al. |
| 6,001,386 A | 12/1999 | Ashton et al. |
| 6,005,079 A | 12/1999 | Casterman et al. |
| 6,019,968 A | 2/2000 | Platz et al. |
| 6,095,141 A | 8/2000 | Armer et al. |
| 6,146,361 A | 11/2000 | DiBiasi et al. |
| 6,170,717 B1 | 1/2001 | Di Giovanni et al. |
| 6,192,891 B1 | 2/2001 | Gravel et al. |
| 6,194,551 B1 | 2/2001 | Idusogie et al. |
| 6,200,296 B1 | 3/2001 | Dibiasi et al. |
| 6,277,099 B1 | 8/2001 | Strowe et al. |
| 6,277,375 B1 | 8/2001 | Ward |
| 6,300,064 B1 | 10/2001 | Knappik et al. |

(Continued)

FOREIGN PATENT DOCUMENTS

| | | |
|---|---|---|
| AU | 2018201961 A1 | 4/2018 |
| EP | 430539 A2 | 6/1991 |

(Continued)

OTHER PUBLICATIONS

Curran, Kevin J et al. "Paroxysmal nocturnal hemoglobinuria in pediatric patients." Pediatric blood & cancer vol. 59,3 (2012): 525-9. doi:10.1002/pbc.23410 (Year: 2012).*

Al-Ani, Fatimah et al. "Eculizumab in the management of paroxysmal nocturnal hemoglobinuria: patient selection and special considerations." Therapeutics and clinical risk management vol. 12 1161-70. Aug. 1, 2016, doi:10.2147/TCRM.S96720 (Year: 2016).*

Greenbaum, L. et al. "Eculizumab is a safe and effective treatment in pediatric patients with atypical hemolytic uremic syndrome" Kidney International, vol. 89: 701-711 (2016).

History of Changes for Study: NCT02949128 Single Arm Study of ALXN1210 in Complement Inhibitor Treatment-Naïve Adult and Adolescent Patients With Atypical Hemolytic Uremic Syndrome (aHUS), Nov. 17, 2022, 6 pages.

(Continued)

*Primary Examiner* — Zachariah Lucas
*Assistant Examiner* — Lia E Taylor
(74) *Attorney, Agent, or Firm* — Nelson Mullins Riley & Scarborough LLP; Jane E. Remillard, Esq.; Jill Gorny Sloper, Esq.

(57) ABSTRACT

Provided are methods for clinical treatment of Paroxysmal Nocturnal Hemoglobinuria (PNH) in pediatric patients using an anti-C5 antibody, or antigen binding fragment thereof.

12 Claims, No Drawings

Specification includes a Sequence Listing.

(56) References Cited

U.S. PATENT DOCUMENTS

| | | |
|---|---|---|
| 6,302,855 B1 | 10/2001 | Lav et al. |
| 6,355,245 B1 | 3/2002 | Evans et al. |
| 6,737,056 B1 | 5/2004 | Presta |
| 6,933,368 B2 | 8/2005 | Co et al. |
| 7,112,341 B1 | 9/2006 | Nagarajan et al. |
| 7,371,826 B2 | 5/2008 | Presta |
| 7,390,786 B2 | 6/2008 | Warne et al. |
| 7,556,615 B2 | 7/2009 | Pettis et al. |
| 7,670,600 B2 | 3/2010 | Dall'Acqua et al. |
| 7,704,497 B2 | 4/2010 | Dall'Acqua et al. |
| 8,088,376 B2 | 1/2012 | Chamberlain et al. |
| 8,323,962 B2 | 12/2012 | Dall'Acqua et al. |
| 8,367,805 B2 | 2/2013 | Chamberlain et al. |
| 8,802,820 B2 | 8/2014 | Chamberlain et al. |
| 9,079,949 B1 * | 7/2015 | Andrien, Jr. ............ A61P 17/06 |
| 9,107,861 B1 | 8/2015 | Andrien, Jr. et al. |
| 9,206,251 B2 | 12/2015 | Andrien, Jr. et al. |
| 9,371,377 B2 | 6/2016 | Andrien, Jr. et al. |
| 9,447,176 B2 | 9/2016 | Rother et al. |
| 9,663,574 B2 | 5/2017 | Andrien, Jr. et al. |
| 9,771,418 B2 | 9/2017 | Rother et al. |
| 9,803,007 B1 | 10/2017 | Andrien, Jr. et al. |
| 10,227,400 B2 | 3/2019 | Andrien, Jr. et al. |
| 10,584,164 B2 | 3/2020 | Andrien, Jr. et al. |
| 11,434,280 B2 | 9/2022 | Andrien, Jr. et al. |
| 12,128,101 B2 | 10/2024 | Payton et al. |
| 2002/0026176 A1 | 2/2002 | Varner et al. |
| 2005/0271660 A1 | 12/2005 | Wang |
| 2006/0141456 A1 | 6/2006 | Edwards et al. |
| 2007/0172483 A1 | 7/2007 | Schwaeble et al. |
| 2007/0235029 A1 | 10/2007 | Zhu et al. |
| 2008/0202513 A1 | 8/2008 | Birchall et al. |
| 2008/0241223 A1 | 10/2008 | Nivaggioli et al. |
| 2009/0110679 A1 | 4/2009 | Li et al. |
| 2010/0098730 A1 | 4/2010 | Lowman et al. |
| 2011/0111406 A1 | 5/2011 | Igawa et al. |
| 2012/0225056 A1 | 9/2012 | Rother et al. |
| 2012/0230982 A1 | 9/2012 | Zhou et al. |
| 2015/0299305 A1 | 10/2015 | Andrien, Jr. et al. |
| 2016/0108115 A1 | 4/2016 | Andrien, Jr. et al. |
| 2016/0251433 A1 | 9/2016 | Andrien, Jr. et al. |
| 2016/0355579 A1 | 12/2016 | Rother et al. |
| 2016/0355580 A1 | 12/2016 | Rother et al. |
| 2017/0298123 A1 | 10/2017 | Andrien, Jr. et al. |
| 2017/0355757 A1 * | 12/2017 | Hu ........................ A61P 21/04 |
| 2017/0369562 A1 | 12/2017 | Rother et al. |
| 2018/0009885 A1 | 1/2018 | Andrien, Jr. et al. |
| 2018/0311299 A1 | 11/2018 | Griffin et al. |
| 2018/0311345 A1 | 11/2018 | Pober et al. |
| 2019/0023775 A1 | 1/2019 | Bachman et al. |
| 2019/0263897 A1 | 8/2019 | Andrien, Jr. et al. |
| 2019/0276524 A1 | 9/2019 | Griffin et al. |
| 2020/0140531 A1 | 5/2020 | Rother et al. |
| 2020/0157200 A1 | 5/2020 | Andrien, Jr. et al. |
| 2020/0254092 A1 | 8/2020 | Payton et al. |
| 2021/0187054 A1 | 6/2021 | Griffin et al. |
| 2021/0332147 A1 | 10/2021 | Payton et al. |
| 2023/0002482 A1 | 1/2023 | Philominathan et al. |
| 2023/0235035 A1 | 7/2023 | Payton et al. |
| 2024/0018220 A1 | 1/2024 | Johnson et al. |
| 2024/0141024 A1 | 5/2024 | Andrien, Jr. et al. |

FOREIGN PATENT DOCUMENTS

| | | |
|---|---|---|
| EP | 488401 A1 | 6/1992 |
| EP | 2006381 A1 | 12/2008 |
| EP | 2275443 A1 | 1/2011 |
| EP | 3095795 A1 | 11/2016 |
| WO | 8902468 A1 | 3/1989 |
| WO | 8905345 A1 | 6/1989 |
| WO | 8907136 A2 | 8/1989 |
| WO | 9207573 A1 | 5/1992 |
| WO | 94/02559 A1 | 2/1994 |
| WO | 94/04678 A1 | 3/1994 |
| WO | 94/28027 A1 | 12/1994 |
| WO | 9734631 A1 | 9/1997 |
| WO | 98/23289 A1 | 6/1998 |
| WO | 98/47531 A2 | 10/1998 |
| WO | 0061178 A1 | 10/2000 |
| WO | 0069887 A2 | 11/2000 |
| WO | 0178693 A2 | 10/2001 |
| WO | 2003/074679 A2 | 12/2003 |
| WO | 03105757 A2 | 12/2003 |
| WO | 2004024156 A1 | 3/2004 |
| WO | 2004026380 A2 | 4/2004 |
| WO | 2004029207 A2 | 4/2004 |
| WO | 2004060407 A1 | 7/2004 |
| WO | 2004073551 A2 | 9/2004 |
| WO | 2005011735 A1 | 2/2005 |
| WO | 2005040217 A2 | 5/2005 |
| WO | 2005/077981 A2 | 8/2005 |
| WO | 2005092925 A2 | 10/2005 |
| WO | 06/031994 | 3/2006 |
| WO | 2006/053301 A2 | 5/2006 |
| WO | 2006094234 A1 | 9/2006 |
| WO | 2006/105338 A2 | 10/2006 |
| WO | 2006/122257 A2 | 11/2006 |
| WO | 2007041635 A2 | 4/2007 |
| WO | 2007/103134 A2 | 9/2007 |
| WO | 2007106585 A1 | 9/2007 |
| WO | 2007114319 A1 | 10/2007 |
| WO | 08/043822 A2 | 4/2008 |
| WO | 2008048545 A2 | 4/2008 |
| WO | 2008092117 A2 | 7/2008 |
| WO | 2009/041643 A1 | 4/2009 |
| WO | 2009058492 A2 | 5/2009 |
| WO | 2009086320 A1 | 7/2009 |
| WO | 2009125825 A1 | 10/2009 |
| WO | 2010/151526 A1 | 12/2010 |
| WO | 2011111007 A2 | 9/2011 |
| WO | 2011122011 A2 | 10/2011 |
| WO | 2011/137362 A1 | 11/2011 |
| WO | 2012/073992 A1 | 6/2012 |
| WO | 2012133782 A1 | 10/2012 |
| WO | 2013046704 A2 | 4/2013 |
| WO | 2013047748 A1 | 4/2013 |
| WO | 2015021166 A2 | 2/2015 |
| WO | 2015/134894 A1 | 9/2015 |
| WO | 2016/098356 A1 | 6/2016 |
| WO | 2016/160756 A1 | 10/2016 |
| WO | 2016/209956 A1 | 12/2016 |
| WO | 2017/044811 A1 | 3/2017 |
| WO | 2017/123636 A1 | 7/2017 |
| WO | 2017/218515 A1 | 12/2017 |
| WO | 2019/084438 A1 | 5/2019 |
| WO | 2019/231983 A1 | 12/2019 |
| WO | 2019/236345 A1 | 12/2019 |
| WO | 2020/092549 A1 | 5/2020 |
| WO | 2020/154626 A1 | 7/2020 |

OTHER PUBLICATIONS

History of Changes for Study: NCT03131219 Study of ALXN1210 in Children and Adolescents With Atypical Hemolytic Uremic Syndrome (aHUS), Nov. 16, 2022, 4 pages.

History of Change for Study: NCT02949128: Single Arm Study of ALXN1210 in Complement Inhibitor Treatment-Naïve Adult and Adolescent Patients with Atypical Hemolytic Syndrome (aHUS); Study NCT02949128, Submitted Date: Oct. 27, 2016 (v1). (2016).

Ito, N. et al., "Efficacy and safety of eculizumab in childhood atypical hemolytic uremic syndrome in Japan," Clin Exp Nephrol., vol. 20:265-272 (2016).

NCT02946463 ALXN1210 Versus Eculizumab in Complement Inhibitor Treatment-Native Adult Patients With Paroxysmal Nocturnal Hemoglobinuria (PNH), ClinicalTrials.gov, [online], Jul. 28, 2017, [retrieved on Jul. 21, 2022], 7 bags https://clinicaltrials.gov/ct2/history/NCT02946463?V_9 View##StudyPageTop>.

Tanaka, K. et al., "The long-acting C5 inhibitor, ravulizumab, is efficacious and safe in pediatric patients with atypical hemolytic uremic syndrome previously treated with eculizumab," Pediatric Nephrology, vol. 36(4):889-898 (2021).

Gupta et al., Vaccine 13(14): 1263-1276 (1995).

Hanauske et al., Clin Cancer Res 13(2, part 1): 523-531 (2007).

(56) References Cited

OTHER PUBLICATIONS

Heinen, S. et al., "Monitoring and modeling treatment of atypical hemolytic uremic syndrome," Molecular Immunology, vol. 54: 84-88 (2013).
Hetherington et al., Antimicrobial Agents and Chemotherapy 50(10): 2499-2500 (2006).
Hezareh et al., J Virol 75: 12161-12168 (2001).
Hillmen et al., N. Engl J Med 350(6): 552-559 (2004).
Hillmen, P. et al., "Long-term safety and efficacy of sustained eculizumab treatment in patients with paroxysmal nocturnal haemoglobinuria," British Journal of Haematology doi: 10.1111/bjh.12347, 12 pages (2013).
Hinton et al., J Biol Chem 279: 6213-6216 (2004).
Hinton et al., J Immunol 176: 346-356 (2006).
Hirt-Minkowski, P. et al., "Atypical Hemolytic Uremic Syndrome: Update on the Complement System and What Is New," Nephron Clin Pract., 114:c219-c235 (2010).
Holers and Thurman, Molecular Immunology 41: 147-152 (2004).
Holers et al., Immunological Reviews 223: 300-316 (2008).
Homeister et al., J Immunol 150: 1055-1064 (1993).
Hou et al., Cytokine 10: 319-30 (1998).
Houdebine, Curr Opin Biotechnol 13(6): 625-629 (2002).
Huber et al., Proc Natl Acad Sci USA 88: 8039-8043 (1991).
Hudson and Kortt, J Immunol Methods 231: 177-189 (1999).
Huston et al., Methods in Enzymology 203: 46-88 (1991).
Hwang et al., Proc Natl Acad Sci USA 77: 4030 (1980).
Hwu et al., J Immunol 150: 4104-4115 (1993).
Igawa et al., "Antibody recycling by engineered pH-dependent antigen binding improves the duration of antigen neutralization," Nat. Biotechnol. 28(11):1203-1207 (2010).
International Preliminary Report on Patentability, PCT/US2018/044071, dated Jan. 28, 2020, 8 pages.
International Preliminary Report on Patentability, PCT/US2018/057760, dated Apr. 28, 2020 2019, 9 pages.
International Preliminary Report on Patentability, PCT/US2019/034293, dated Dec. 1, 2020, 9 pages.
International Preliminary Report on Patentability, PCT/US2019/034297, dated Dec. 8, 2020, 10 pages.
International Search Report and Written Opinion for Application No. PCT/US2015/019225, dated May 18, 2015.
International Search Report and Written Opinion, PCT/US2018/044071, dated Oct. 2, 2018, 12 pages.
International Search Report and Written Opinion, PCT/US2018/057760, dated Mar. 21, 2019, 13 pages.
International Search Report and Written Opinion, PCT/US2019/034293, dated Aug. 21, 2019, 14 pages.
International Search Report and Written Opinion, PCT/US2019/034297, dated Sep. 25, 2019, 13 pages.
International Search Report and Written Opinion, PCT/US2020/014998, dated Jun. 22, 2020, 13 pages.
Isaacs et al., J Immunol 161: 3862-3869 (1998).
Isenman et al., J Immunol 124: 326-331 (1980).
Ishii-Watabe, A. et al., "Molecular Design of Therapeutic Antibodies," Pharmaceutics 74 (1): 4-11: 17 pages (2014).
Israel et al, Immunology 89(4): 573-578 (1996).
Ito, W et al., "The His-probe method: effects of histidine residues introduced into the complementarity-determining regions of antibodies on antigen-antibody interactions at different pH values," FEBS Letter, vol. 309(1): 85-88(1992).
Johne et al., J Immunol Meth 160: 191-198 (1993).
Johnson et al., J Med Chem 42: 4640-4649 (1999).
Jones et al., Nature 321: 522-525 (1986).
Jonsson et al., Ann Biol Clin 51: 19-26 (1993).
Jonsson et al., Biotechniques 11: 620-627 (1991).
Junghans, R. et al., "The protection receptor for IgG catabolism is the beta2-microglobulin-containing neonatal Intestinal transport receptor," PNAS, USA, vol. 93(11):512-5516 (1996).
Jungi and Pepys, Immunology 43(2): 271-279 (1981).
Kaszubska et al., Protein Expression and Purification 18: 213-220 (2000).

Kay et al., Human Gene Therapy 3: 641-647 (1992).
Kim et al., Ophthalmic Res 39: 244-254 (2007).
Kinstler et al., Advanced Drug Deliveries Reviews 54: 477-485.
Klein et al., Proc. Natl Acad Sci USA 78: 524-528 (1981).
Kroshus et al., Transplantation 60: 1194-1202 (1995).
Lee, CV., et al., "High-affinity human antibodies from phage-displayed synthetic Fab libraries with a single framework scaffold," J. Molecular Biology, vol. 340 (5):1073-1093 (2004).
Lee, et al., Bioconjug Chem 10(6): 973-81 (1999).
Lee, J-W et al., "Results from a Phase 3, Multicenter, Noninferiority Study of Ravulizumab (ALXN1210) Versus Eculizumab in Adult Patients with Paroxysmal Nocturnal Hemoglobi-nuria (PNH) Naïve to Complement Inhibitors," (2018), XP055550310, Retrieved from the Internet: URL:https://learningcenter.ehaweb.org/eha/2018/stockholm/218885/jong.wook.lee.results.from.a.phase.3.multicenter.noninferiority.study.of.html?f=media=1 [retrieved on Jan. 31, 2019].
Lee, J-W et al., "Ravulizumab (ALXN1210) vs eculizumab in adult patients with PNH naive to complement inhibitors: the 301 study," Blood, (2018) ISSN: 0006-4971, DOI: 10.1182/blood-2018-09-876136.
Lee, J-W. et al., "2428 Immediate, Complete, and Sustained Inhibition of C5 with ALXN1210 Reduces Complement-Mediated Hemolysis in Patients with Paroxysmal Noctur-nal Hemoglobinuria (PNH): Interim Analysis of a Dose-Escalation Study," Internet Ci-Tation, Dec. 4, 2016 (Dec. 4, 2016), XP002768543, Retrieved from the Internet: URL:https://ash.confex.com/ash/2016/webprogram/Paper90053.html [retrieved on Mar. 23, 2017] the whole document.
Legendre, CM, et al., "Terminal Complement Inhibitor Eculizumab in Atypical Hemolytic-Uremic Syndrome," N Engl J Med., vol. 368:2169-2181 (2013).
Levy and Ladda, Nat New Biol 229(2): 51-52 (1971).
Licht, C., et al., "The global aHUS registry: methodology and initial patient characteristics," BMC Nephrology, vol. 16 (207) 8 pages (2015) DOI 10.1186/s12882-015-0195-1.
Lodmell et al., Vaccine 18:1059-1066 (2000).
Loirat, , C. et al., "Plasmatherapy in Atypical Hemolytic Uremic Syndrome," Seminars in Thrombosis and Hemostasis, vol. 36(6): 673-681 (2010).
Loirat, C. et al., "An international consensus approach to the management of atypical hemolytic uremic syndrome in children," Pediatr Nephrol., vol. 31:15-39 (2016).
Loirat, C. et al., "Atypical hemolytic uremic syndrome," Orphanet Journal of Rare Diseases, vol. 6:60: 30 pages (2011).
Lusky and Botchan, Nature 293: 79 (1981).
Malina, M. et al., "Peripheral Gangrene in Children With Atypical Hemolytic Uremic Syndrome," Pediatrics, vol. 131: e331-e335 (2013).
McLaughlin et al., J Virol 62: 1963-1973 (1989).
Medicus et al., J Exp Med 144: 1076-1093 (1976).
Mihu et al., J Gastrointestin Liver Dis 16(4): 419-424 (2007).
Moongkarndi et al, Immunobiol 165: 323 (1983).
Moongkarndi et al., Immunobiol 162: 397 (1982).
Morell et al., J Clin Invest 49(4): 673-680 (1970).
Mueller et al., Mol Immunol 34(6): 441-452 (1997).
Muller-Eberhard, Ann Rev Biochem 57: 321-347 (1988).
Mullett et al., Methods 22: 77-91 (2000).
Mulligan and Berg Proc Natl Acad Sci USA 78: 2072 (1981).
Mullinax et al., BioTechniques 12(6): 864-869 (1992).
Muyldermans et al., Trends Biochem Sci 26: 230-235 (2001).
Newkirk et al., Clin Exp Immunol 106(2): 259-264 (1996).
Noris, M. et al., "STEC-HUS, atypical HUS and TTP are all diseases of complement activation," Nat. Rev. Nephrol., vol. 8: 622-633 (2012).
Nuttall et al., Curr Pharm Biotech 1: 253-263 (2000).
Park et al., Anesth Analg 99(1): 42-48 (1999).
Pavisic et al., Int J Pharm 387(1-2)L 110-119 (2010).
Petkova et al., Int Immunol 18(12): 1759-69 (2006).
Poljak, Structure 2(12): 1121-1123 (1994).
Pollock et al., J Immunol Methods 231(1-2): 147-157 (1999).
Qiao et al., Proc Natl Acad Sci USA 105(27): 9337-9342 (2008).
Rabinovici et al., J Immunol 149 1744-1750 (1992).
Raju, BioProcess International 1(4): 44-53 (2003).
Ranta and Uritti, Adv Drug Delivery Rev 58(11): 1164-1181 (2006).

(56) References Cited

OTHER PUBLICATIONS

Rawal and Pangburn, J Immunol 166(4): 2635-2642 (2001).
Reiss, U. et al., "Efficacy and safety of eculizumab in children and adolescents with paroxysmal nocturnal hemoglobinuria," Pediatric Blood and Cancer, vol. 61(9):1544-1550 (2014).
Rich et al., Curr Opin Biotechnol 11: 54-61 (2000).
Riechmann et al., J Immunol Meth 231: 25-38 (1999).
Riechmann et al., Nature 332: 323-327 (1988).
Rinder et al., J Clin Invest 96: 1564-1572 (1995).
Roberts et al., Advanced Drug Delivery Reviews 54: 459-476 (2002).
Roeth, A. et al., "Optimization of Dose Regimen for ALXN1210, a Novel Complement C5 Inhibitor, in Patients with Paroxysmal Nocturnal Hemoglobinuria (PNH):Results of 2 Phase 1/2 Studies," Blood, vol. 130:3482 (2017).
Rogers et al., J Nucl Med 38: 1221-1229 (1997).
Rondeau, E. et al., "The long-acting C5 inhibitor, Ravulizumab, is effective and safe in adult patients with atypical hemolytic uremic syndrome naive to complement inhibitor treatment," Kidney International, Mar. 6, 2020, pp. 1-10.
Rondon and Marasco, Annual Review of Microbiology 51: 257-284 (1997).
Roopenian et al., Methods Mol Biol 602: 93-104 (2010).
Roopenian, DC, et al., "FcRn: the neonatal Fc receptor comes of age," Nature Reviews Immunology, vol. 7(9): 115-725 (2007).
International Search Report and Written Opinion, PCT/US2021/040802, dated Oct. 18, 2021, 9 pages.
U.S. Appl. No. 18/011,807, filed Dec. 20, 2022, Lori Payton, US 20230235035.
U.S. Appl. No. 16/750,173, filed Jan. 23, 2020, Bruce A. Andrien.
U.S. Appl. No. 16/246,842, filed Jan. 14, 2019, Bruce A. Andrien.
U.S. Appl. No. 15/708,658, filed Sep. 19, 2017, Bruce A. Andrien.
U.S. Appl. No. 15/492,622, filed Apr. 20, 2017, Bruce A. Andrien.
U.S. Appl. No. 15/160,364, filed May 20, 2016, Bruce A. Andrien.
U.S. Appl. No. 14/923,879, filed Oct. 27, 2015, Bruce A. Andrien.
U.S. Appl. No. 14/789,329, filed Jul. 1, 2015, Bruce A. Andrien.
U.S. Appl. No. 14/727,313, filed Jun. 1, 2015, Bruce A. Andrien.
U.S. Appl. No. 14/641,026, filed Mar. 6, 2015, Bruce A. Andrien.
U.S. Appl. No. 16/757,512, filed Apr. 20, 2020, Lori Payton.
U.S. Appl. No. 17/057,898, filed Nov. 23, 2020, Lori Payton.
U.S. Appl. No. 16/246,842, Oct. 25, 2019.
U.S. Appl. No. 16/246,842, Jun. 14, 2019.
U.S. Appl. No. 15/708,658, Oct. 22, 2018.
U.S. Appl. No. 15/708,658, Jun. 25, 2018.
U.S. Appl. No. 15/492,622, Sep. 14, 2017.
U.S. Appl. No. 15/492,622, Aug. 24, 2017.
U.S. Appl. No. 15/160,364, Feb. 7, 2017.
U.S. Appl. No. 15/160,364, Dec. 2, 2016.
U.S. Appl. No. 15/160,364, Sep. 14, 2016.
U.S. Appl. No. 14/923,879, May 16, 2016.
U.S. Appl. No. 14/923,879, Apr. 4, 2016.
U.S. Appl. No. 14/923,879, Feb. 23, 2016.
U.S. Appl. No. 14/923,879, Feb. 5, 2016.
U.S. Appl. No. 14/789,329, Sep. 25, 2015.
U.S. Appl. No. 14/727,313, Jun. 22, 2015.
U.S. Appl. No. 14/641,026, May 29, 2015.
U.S. Appl. No. 14/641,026, May 13, 2015.
Ambati and Adamis, Prog Retin Eye Res 21(2): 145-151 (2002).
Amsterdam et al., Am J Physiol 268: H448-H457 (1995).
Anonymous: "Alexion Receives FDA Approval for ULTOMIRIS (ravulizumab-cwvz) for Atypical Hemolytic Uremic Syndrome (aHUS)," Oct. 18, 2019.
Anonymous: "Assessment report Soliris /Eculizumab," pp. 1-28, Mar. 21, 2013, Retrieved from the Internet: URL: https://www.ema.europa.eu/en/documents/variation-report/soliris-h-c-791-ii-0050-epar-assessment-report-variation_en.pdf [retrieved on Aug. 7, 2019].
Anonymous: "Ravulizumab for atypical haemolytic uraemic syndrome in adults and children—first line," Aug. 1, 2018, pp. 1-10.
Anonymous: "Single Arm Study of ALXN1210 in Complement Inhibitor Treatment-Naive Adult and Adolescent Patients With Atypical Hemolytic Uremic Syndrome (aHUS)," pp. 1-6 (2016) XP055619305, Retrieved from the Internet:URL: https://clinicaltrials.gov/ct2/show/NCT02949128?term=alxn1210&rank=8 [retrieved on Sep. 6, 2019].
Anonymous: "Study of ALXN1210 in Children and Adolescents With Atypical Hemolytic Uremic Syndrome (aHUS)", Apr. 27, 2017 (Apr. 27, 2017), pp. 1-9, XP055619309, Retrieved from the Internet: URL:https://clinicaltrials.gov/ct2/show/NCT03131219?term=alxn1210&rank=5 [retrieved on Sep. 6, 2019].
Appel et al., J Am Soc Nephrol 16: 1392-1404 (2005).
Armentano et al., Proc Natl Acad Sci USA 87: 6141-6145 (1990).
Baldridge et al., Methods 19: 103-107 (1999).
Barocas and Balachandran, Expert Opin Drug Delivery 5(1): 1-10 (10) (2008).
Baudino et al.l, J Immunol 181: 6664-6669 (2008).
Berge et al., J Phar4m Sci 66: 1-19 (1977).
Berkner et al., Bio Techniques 6: 616 (1988).
Better et al., Science 240: 1041-1043 (1988).
Bieg et al., Autoimmunity 31(1): 15-24 (1999).
Bless et al., Am J Physiol 276(1): L57-L63 (1999).
Brodsky, R. et al., "Complement in hemolytic anemia," Blood, vol. 126(22):2459-2465 (2015).
Burmeister et al., Nature 372: 379-383 (1994).
Burton et al., Adv Immun 51:1-18 (1992).
Campistol, J., et al., "An update for atypical haemolytic uraemic syndrome: diagnosis and treatment. A consensus document," Nefrologia, vol. 33(1):27-45 (2013).
Canfield et al., J Exp Med 173: 1483-1491 (1991).
Caron et al., J Exp Med 176: 1191-1195 (1992).
Chaparro-Riggers, Biol Chem 287: 11090-11097 (2012).
Chothia et al., Nature 342: 877-883 (1989).
Chowdhury et al., Science 254: 1802-1805 (1991).
Christmann, M., et al., "Eculizumab as First-Line Therapy for Atypical Hemolytic Uremic Syndrome," Pediatrics, vol. 133, e1759: 7 pages (2014).
Co et al., Mol Immunol 30: 1361 (1993).
Cooper et al., J Exp Med 132: 775-793 (1970).
Crocker et al., J Clin Pathol 27(2): 122-124 (1974).
Dai et al., Proc Natl Acad Sci USA 89: 10892-10895 (1992).
Dall'Acqua et al., J Biol Chem 281: 23514-23524 (2006).
Dall'Acqua et al., J Immunol 117: 1129-1138 (2006).
Danos and Mulligan, Proc Natl Acad Sci USA 85; 6460-6464 (1988).
Datta-Mannan et al., J Biol Chem 282(3): 1709-1717 (2007).
Daugherty, A., et al., "Formulation and delivery issues for monoclonal antibody thera-peutics," Current Trends in Monoclonal Antibody Development and Manufacture, Chapter 8:103-129 (2010).
Deans et al., Proc Natl Acad Sci USA 81: 1292 (1984).
Dong et al, Reviews in Mol Biotech 82: 303-323 (2002).
Duncan and Winter Nature 322: 738-40 (1988).
Eglitis et al., Science 230: 1395-1398 (1985).
Epstein et al., Proc Natl Acad Sci USA 82: 3688 (1985).
European Search Report, EP Application No. 161776562, dated Aug. 8, 2016, 8 pages.
Evans, et al., Mol Immunol 32(16): 1183-95 (1995).
Fakhouri, F. et al., "Terminal Complement Inhibitor Eculizumab in Adult Patients With Atypical Hemolytic Uremic Syndrome: A Single-Arm, Open-Label Trial," Am J Kidney Dis., vol. 68(1):84-93 (2016).
Fearon et al., J Exp Med 142: 856-863 (1975).
Ferry et al., Proc Natl Acad Sci USA 88: 8377-8381 (1991).
Fivash et al., Curr Opin Biotechnol 9: 97-101 (1998).
Flotte et al., Am J Respir Cell Mol Biol 7: 349-356 (1992).
Ghetie et al., Nat Biotech 15: 637-640 (1997).
Gulsen and Chauhan, Invest Opthalmol Vis Sci 45: 2342-2347 (2004).
Yuksel, S. et al., "First-Line, Early and Long-Term Eculizumab Therapy in Atypical Hemolytic Uremic Syndrome: A Case Series in Pediatric Patients," Pediatr Drugs, vol. 18:413-420 (2016) DOI 10.1007/s40272-016-0194-0.
Zalevsky et al., Nat Biotech 28: 157-159 (2010).
Zuber, J. et al., "new insights into postrenal transplant hemolytic uremic syndrome," Nat. Rev. Nephrol., vol. 7: 23-35 (2011).

(56) References Cited

OTHER PUBLICATIONS

Chonat, S. et al., "Pharmacokinetics, pharmacodynamics, efficacy, and safety of ravulizumab in pediatric paroxysmal nocturnal hemoglobinuria," Blood Adv., vol. 8(11):2813-2824 (2024).
Rosenfeld et al., Cell 68: 143-155 (1992).
Roth, A. et al., "Ravulizumab (ALXN1210) in patients with par-oxysmal nocturnal hemo-globinuria: results of phase b/2 studies", Blood Adv., vol. 2 (17): 2176-2185 (2018).
Rother, R. et al.,"Discovery and development of the complement inhibitor eculizumab for the treatment of paroxysmal nocturnal hemoglobinuria," Nature Biotechnology, 25 (11): 1256-1264 (1488 Supp) (2007).
Rother et al., Nature Biotechnology 25 (11): 1256-1263 (2007).
Saland, J. et al., "Liver-kidney transplantation to cure atypical HUS: still an option post-eculizumab?," Pediatr Nephrol., DOI 10.1007/s00467-013-2722-2, 4 pages (2013).
Salvadori, M. et al., "Update on hemolytic uremic syndrome: Diagnostic and therapeutic recommendations," World J Nephrol., vol. 2(3): 56-76 (2013).
Samulski et al., J Virol 63: 3822-3828 (1989).
Sarkar, C.,A., et al., "Rational cytokine design for increased lifetime and enhanced potency using pH-activated histidine switching," Nature Biotechnology, vol. 20(9):908-913 (2002).
Sarver et al., Proc Natl Acad Sci USA 79: 7147 (1982).
Sawai et al., Am J Repr Immunol 34: 26-34 (1995).
Schmid et al., Schock 8(2): 119-124 (1997).
Schoonbroodt et al., Nucleic Acids Res 33(9): e81 (2005).
Schreiber et al., Proc Natl Acad Sci USA 75: 3948-3952 (1978).
Scully, M. et al., "Systemic Involvement at Entry into the Global Atypical Hemolytic Uremic Syndrome (aHUS) Registry," Blood, vol. 128:3729 6 pages (2016).
Sharma, V.K. et al., "The formulation and delivery of monoclonal antibodies", Therapeutic Monoclonal Antibodies, Chapter 30: 675-711 (2009).
Sheerin, N.S. et al., "A national specialized service in England for atypical haemolytic uraemic syndrome-the first year's experience," QJM: An International Journal of Medicine, 27-33: 7 pages (2016).
Sheridan, D. et al., "Design and preclinical characterization of ALXN1210: A next generation anti-C5 monoclonal antibody with improved pharmacokinetics and duration of action," Immunobiology, vol. 221(Issue 10): 1158 (2016).
Sheridan, D. et al., "Design and preclinical characterization of ALXN1210: A novel anti-C5 antibody with extended duration of action," PLoS One 13(4): e0195909, 15 pages (2018).
Sheridan, D. et al., "Design and preclinical characterization of ALXN1210: A novel anti-05 antibody with extended duration of action", PLOS One, vol. 13(4):e0195909 (2018).
Shields et al., J Biol Chem 276(9): 6591-6604 (2001).
Shields et al., J Biol Chem 277(30): 26733-26740 (2002).
Shire, S. et al., "High-concentration antibody formulations," Formulation and Process De-velopment Strategies for Manufacturing Biopharmaceuticals, Chapter 15: 349-381 (2010).
Shopes, Immunol 148: 2918-2922 (1992).
Shu et al., Proc Natl Aced Sci USA 90: 7995-7999 (1993).
Sissons et al., Proc Natl Acad Sci USA 77: 559-562 (1980).
Skerra et al., Science 240: 1038-1040 (1988).
Southern and Berg, Mol Appl Genet 1:327 (1982).
Staelens et al., Mol Immunol 43: 1243-1257 (2006).
Tabrizi, Ma et al., "Elimination mechanisms of therapeutic monoclonal antibodies ," Drug Discovery Today, vol. 11 (1-2):81-88 (2006).
Thomas et al., Mol Immunol 33(17118): 1389-1401 (1996).
Todorovska et al., J Immunol Methods 248(1): 47-66 (2001).
Tofukuji et al., J Thorac Cardiovasc Surg 166(6): 1060-1068 (1998).
Tsai, H. et al., "A Mechanistic Approach to the Diagnosis and Management of Atypical Hemolytic Uremic Syndrome," Transfusion Medicine Reviews, vol. 28:187-197 (2014).
van Beusechem et al., Proc Natl Acad Sci USA 89: 7640-7644 (1992).
van Gurp et al., Am J Transplantation 8(8): 1711-1718 (2008).
van Kuik-Romeijn et al., Transgenic Res 9(2): 155-159 (2000).
Verhoeyen et al., Science 239: 1534-1536 (1988).
Wang et al., Proc Natl Acad Sci USA 93: 8563-8568 (1996).
Wang et al.,Proc Natl Acad Sci USA 92: 8955-8959 (1995).
Wang, W. et al., "Antibody Structure, Instability, and Formulation," Journal of Pharmaceutical Sciences, American Chemical Society and American Pharmaceutical Association, vol. 96(1):1-26 (2007).
Ward and Zvaifler, J Clin Invest 50(3): 606-16 (1971).
Waters, A. et al., "aHUS caused by complement dysregulation: new therapies on the horizon," Pediatr Nephrol., vol. 26:41-57 (2011).
Weisman et al., Science 249: 146-151 (1990).
Wetsel et al., J Biol Chem 265: 2435-2440 (1990).
Wigler et al., Cell 16: 77 (1979).
Wilson et al., Proc Natl Acad Sci USA 85: 3104-3018 (1988).
Wong, E. et al., "Anticomplement C5 therapy with eculizumab for the treatment of parox-ysmal nocturnal hemoglobinuria and atypical hemolytic uremic syndrome," Translational Research, vol. 165 (2): 306-320 (2017) XP055358380, NL ISSN: 1931-5244, DOI:10.1016/j.trsl.2014.10.010.
Wright et al., EMBO J 10(10): 2717-2723 (1991).
Wurzner et al., Complement Inflamm 8: 328-340 (1991).
Xu et al, Cell Immunol 200: 16-26 (2000).

\* cited by examiner

DOSAGE AND ADMINISTRATION OF ANTI-C5 ANTIBODIES FOR TREATMENT OF PAROXYSMAL NOCTURNAL HEMOGLOBINURIA (PNH) IN PEDIATRIC PATIENTS

CROSS-REFERENCE TO RELATED APPLICATIONS

This application is a 35 U.S.C. 371 national stage filing of International Application No. PCT/US2019/034293, filed May 29, 2019, which claims priority to, and the benefit of, U.S. Provisional Application No. 62/678,455, filed May 31, 2018. The entire contents of the aforementioned applications are incorporated herein by reference.

SEQUENCE LISTING

The instant application contains a Sequence Listing that has been submitted electronically in ASCII format and is hereby incorporated by reference in its entirety. Said ASCII copy, created on Nov. 23, 2020, is named AXJ-245US_Sequence_Listing.txt and is 50,658 bytes in size.

BACKGROUND

Paroxysmal nocturnal hemoglobinuria (PNH) is a progressive, debilitating, and life-threatening disease characterized by complement-mediated hemolysis, thrombosis and bone marrow failure. PNH has an estimated worldwide incidence of 1.3 per million population. The onset of PNH is typically in adulthood, with pediatric cases accounting for <5% of reported cases. Given the extremely small target population, studies of children with PNH have been limited to case reports, case series, and a small clinical trial.

In adults, the clinical manifestations of PNH include hemoglobinuria, chronic renal insufficiency, erectile dysfunction, thrombosis, abdominal pain, dyspnea and dysphagia. In contrast, children with PNH usually present with nonspecific symptoms related to the underlying bone marrow disorder, such as pallor, fatigue or jaundice, with hemoglobinuria appearing less commonly. Clinical evaluation in pediatric patients also reveals bone marrow failure syndromes, such as aplastic anemia and refractory cytopenia. Once the bone marrow disorder is resolved in the child or the PNH clone expands (the cause of which is still unknown), the disease eventually evolves into one more typically seen in adults at presentation.

Thus, pediatric patients can be expected to suffer substantial morbidity related to hemolysis, as seen in adult PNH patients. Accordingly, it is an object of the present disclosure to provide improved methods for treating patients with PNH.

SUMMARY

Provided herein are compositions and methods for treating Paroxysmal Nocturnal Hemoglobinuria (PNH) in a human pediatric patient, comprising administering to the patient an anti-C5 antibody or antigen binding fragment thereof, wherein the anti-C5 antibody or antigen binding fragment thereof is administered (or is for administration) according to a particular clinical dosage regimen (e.g., at a particular dose amount and according to a specific dosing schedule).

An exemplary anti-C5 antibody is ravulizumab comprising the heavy and light chains having the sequences shown in SEQ ID NOs:14 and 11, respectively, or antigen binding fragments and variants thereof. In other embodiments, the antibody comprises the heavy and light chain complementarity determining regions (CDRs) or variable regions (VRs) of ravulizumab. Accordingly, in one embodiment, the antibody comprises the CDR1, CDR2 and CDR3 domains of the heavy chain variable (VH) region of ravulizumab having the sequence shown in SEQ ID NO:12, and the CDR1, CDR2 and CDR3 domains of the light chain variable (VL) region of ravulizumab having the sequence shown in SEQ ID NO:8. In another embodiment, the antibody comprises CDR1, CDR2 and CDR3 heavy chain sequences as set forth in SEQ ID NOs:19, 18 and 3, respectively, and CDR1, CDR2 and CDR3 light chain sequences as set forth in SEQ ID NOs:4, 5 and 6, respectively. In another embodiment, the antibody comprises VH and VL regions having the amino acid sequences set forth in SEQ ID NO:12 and SEQ ID NO:8, respectively. In another embodiment, the antibody comprises a heavy chain constant region as set forth in SEQ ID NO:13.

In another embodiment, the antibody comprises a variant human Fc constant region that binds to human neonatal Fc receptor (FcRn), wherein the variant human Fc CH3 constant region comprises Met429Leu and Asn435Ser substitutions at residues corresponding to methionine 428 and asparagine 434 of a native human IgG Fc constant region, each according to the EU numbering convention.

In another embodiment, the antibody comprises CDR1, CDR2 and CDR3 heavy chain sequences as set forth in SEQ ID NOs:19, 18 and 3, respectively, and CDR1, CDR2 and CDR3 light chain sequences as set forth in SEQ ID NOs:4, 5 and 6, respectively and a variant human Fc constant region that binds to human neonatal Fc receptor (FcRn), wherein the variant human Fc CH3 constant region comprises Met429Leu and Asn435Ser substitutions at residues corresponding to methionine 428 and asparagine 434 of a native human IgG Fc constant region, each according to the EU numbering convention.

In another embodiment, the anti-C5 antibody comprises the heavy and light chain CDRs or variable regions of the BNJ421 antibody (described in PCT/US2015/019225 and U.S. Pat. No. 9,079,949). In another embodiment, the anti-C5 antibody comprises the heavy and light chain CDRs or variable regions of the 7086 antibody (see U.S. Pat. Nos. 8,241,628 and 8,883,158). In another embodiment, the anti-C5 antibody comprises the heavy and light chain CDRs or variable regions of the 8110 antibody (see U.S. Pat. Nos. 8,241,628 and 8,883,158). In another embodiment, the anti-C5 antibody comprises the heavy and light chain CDRs or variable regions of the 305LO5 antibody (see US2016/0176954A1). In another embodiment, the anti-C5 antibody comprises the heavy and light chain CDRs or variable regions of the SKY59 antibody.

In another embodiment, the antibody competes for binding with, and/or binds to the same epitope on C5 as any of the above-mentioned antibodies. In another embodiment, the antibody has at least about 90% variable region amino acid sequence identity to any of the above-mentioned antibodies (e.g., at least about 90%, 95% or 99% variable region identity with SEQ ID NO:12 or SEQ ID NO:8).

In another embodiment, the antibody binds to human C5 at pH 7.4 and 25 C with an affinity dissociation constant ($K_D$) that is in the range 0.1 nM≤$K_D$≤1 nM. In another embodiment, the antibody binds to human C5 at pH 6.0 and 25 C with a $K_D$≥10 nM. In yet another embodiment, the [($K_D$ of the antibody or antigen-binding fragment thereof for human C5 at pH 6.0 and at 25 C)/($K_D$ of the antibody or antigen-binding fragment thereof for human C5 at pH 7.4 and at 25 C)] of the antibody is greater than 25.

In one embodiment, the dose of the anti-C5 antibody, or antigen binding fragment thereof, is based on the weight of the patient. In one embodiment, for example, 300 mg of the anti-C5 antibody or antigen binding fragment thereof is administered to a patient weighing ≥5 to <10 kg. In another embodiment, 600 mg of the anti-C5 antibody or antigen binding fragment thereof is administered to a patient weighing ≥10 to <20 kg. In another embodiment, 900 mg or 2100 mg of the anti-C5 antibody or antigen binding fragment thereof is administered to a patient weighing ≥20 to <30 kg. In another embodiment, 1200 mg or 2700 mg of the anti-C5 antibody or antigen binding fragment thereof is administered to a patient weighing ≥30 to <40 kg. In another embodiment, 2400 mg or 3000 mg of the anti-C5 antibody or antigen binding fragment thereof is administered to a patient weighing ≥40 to <60 kg. In another embodiment, 2700 mg or 3300 mg of the anti-C5 antibody or antigen binding fragment thereof is administered to a patient weighing ≥60 to <100 kg. In another embodiment, 3000 mg or 3600 mg of the anti-C5 antibody or antigen binding fragment thereof is administered to a patient weighing ≥100 kg. In certain embodiments, dosage regimens are adjusted to provide the optimum desired response (e.g., an effective response).

In another embodiment, the anti-C5 antibody or antigen binding fragment thereof is administered for one or more administration cycles. In one embodiment, the treatment (e.g., administration cycle) is 26 weeks. In one embodiment, the anti-C5 antibody or antigen binding fragment thereof is administered once on Day 1 (e.g., of the administration cycle), once on Day 15 (e.g., of the administration cycle), and every four weeks thereafter. In another embodiment, the anti-C5 antibody or antigen binding fragment thereof is administered once on Day 1 (e.g., of the administration cycle), once on Day 15 (e.g., of the administration cycle), and every eight weeks thereafter. In another embodiment, the anti-C5 antibody or antigen binding fragment thereof is administered every four or eight weeks after treatment (e.g., an administration cycle) for an extension period up to two years (e.g., at a dose of 300 mg, 600 mg, 900 mg, 1200 mg, 2100 mg, 2400 mg, 2700 mg, 3000 mg, 3300 mg or 3600 mg).

In another embodiment, a method of treating a human patient with PNH is provided, the method comprising administering to the patient (e.g., during an administration cycle) an effective amount of an anti-C5 antibody or antigen binding fragment thereof, comprising CDR1, CDR2 and CDR3 heavy chain sequences as set forth in SEQ ID NOs:19, 18 and 3, respectively, and CDR1, CDR2 and CDR3 light chain sequences as set forth in SEQ ID NOs:4, 5 and 6, respectively, wherein the anti-C5 antibody or antigen binding fragment thereof is administered: (a) once on Day 1 at a dose of 600 mg to a patient weighing ≥5 to <10 kg, 600 mg to a patient weighing ≥10 to <20 kg, 900 mg to a patient weighing ≥20 to <30 kg, 1200 mg to a patient weighing ≥30 to <40 kg, 2400 mg to a patient weighing ≥40 to <60 kg, 2700 mg to a patient weighing ≥60 to <100 kg, or 3000 mg to a patient weighing ≥100 kg; and (b) on Day 15 and every four weeks thereafter at a dose of 300 mg to a patient weighing ≥5 to <10 kg or 600 mg to a patient weighing ≥10 to <20 kg; or on Day 15 and every eight weeks thereafter at a dose of 2100 mg to a patient weighing ≥20 to <30 kg, 2700 mg to a patient weighing ≥30 to <40 kg, 3000 mg to a patient weighing ≥40 to <60 kg, 3300 mg to a patient weighing ≥60 to <100 kg, or 3600 mg to a patient weighing ≥100 kg.

In another embodiment, a method of treating a human patient with PNH is provided, the method comprising administering to the patient (e.g., during an administration cycle) an effective amount of an anti-C5 antibody or antigen binding fragment thereof comprising CDR1, CDR2 and CDR3 heavy chain sequences as set forth in SEQ ID NOs:19, 18 and 3, respectively, CDR1, CDR2 and CDR3 light chain sequences as set forth in SEQ ID NOs:4, 5 and 6, respectively, and a variant human Fc constant region that binds to human neonatal Fc receptor (FcRn), wherein the variant human Fc CH3 constant region comprises Met429Leu and Asn435Ser substitutions at residues corresponding to methionine 428 and asparagine 434 of a native human IgG Fc constant region, each according to the EU numbering convention, wherein the anti-C5 antibody or antigen binding fragment thereof is administered: (a) once on Day 1 at a dose of 600 mg to a patient weighing ≥5 to <10 kg, 600 mg to a patient weighing ≥10 to <20 kg, 900 mg to a patient weighing 20 to <30 kg, 1200 mg to a patient weighing ≥30 to <40 kg, 2400 mg to a patient weighing 40 to <60 kg, 2700 mg to a patient weighing 60 to <100 kg, or 3000 mg to a patient weighing 100 kg; and (b) on Day 15 and every four weeks thereafter at a dose of 300 mg to a patient weighing 5 to <10 kg or 600 mg to a patient weighing 10 to <20 kg; or on Day 15 and every eight weeks thereafter at a dose of 2100 mg to a patient weighing 20 to <30 kg, 2700 mg to a patient weighing ≥30 to <40 kg, 3000 mg to a patient weighing 40 to <60 kg, 3300 mg to a patient weighing 60 to <100 kg, or 3600 mg to a patient weighing 100 kg.

In another embodiment, the anti-C5 antibody or antigen binding fragment thereof is administered to a patient weighing 5 to <10 kg: (a) once on Day 1 at a dose of 600 mg; and (b) on Day 15 and every four weeks thereafter at a dose of 300 mg.

In another embodiment, the anti-C5 antibody is administered to a patient weighing ≥10 to <20 kg: (a) once on Day 1 at a dose of 600 mg; and (b) on Day 15 and every four weeks thereafter at a dose of 600 mg.

In another embodiment, the anti-C5 antibody is administered to a patient weighing ≥20 to <30 kg: (a) once on Day 1 at a dose of 900 mg; and (b) on Day 15 and every eight weeks thereafter at a dose of 2100 mg.

In another embodiment, the anti-C5 antibody is administered to a patient weighing ≥30 to <40 kg: (a) once on Day 1 at a dose of 1200 mg; and (b) on Day 15 and every eight weeks thereafter at a dose of 2700 mg.

In another embodiment, the anti-C5 antibody is administered to a patient weighing ≥40 to <60 kg: (a) once on Day 1 at a dose of 2400 mg; and (b) on Day 15 and every eight weeks thereafter at a dose of 3000 mg.

In another embodiment, the anti-C5 antibody is administered to a patient weighing ≥60 to <100 kg: (a) once on Day 1 at a dose of 2700 mg; and (b) on Day 15 and every eight weeks thereafter at a dose of 3300 mg.

In another embodiment, the anti-C5 antibody is administered to a patient weighing ≥100 kg: (a) once on Day 1 at a dose of 3000 mg; and (b) on Day 15 and every eight weeks thereafter at a dose of 3600 mg.

In one embodiment, the patient has not previously been treated with eculizumab. In another embodiment, the patient has previously been treated with eculizumab. In another embodiment, the patient has previously been treated with eculizumab and Day 1 (e.g., of the administration cycle) is two weeks or more from the patient's last dose of eculizumab.

In another aspect, the treatment regimens described are sufficient to maintain particular serum trough concentrations of the anti-C5 antibody or antigen binding fragment thereof. In one embodiment, for example, the treatment regimen maintains a serum trough concentration of the anti-C5 antibody or antigen binding fragment thereof of 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 240, 245, 250, 255, 260, 265, 270, 280, 290, 300, 305, 310, 315, 320, 325, 330, 335, 340, 345, 350, 355, 360, 365, 370, 375, 380, 385, 390, 395 or 400 μg/mL or greater. In one embodiment, the treatment regimen maintains a serum trough concentration of the anti-C5 antibody or antigen binding fragment thereof of 100 μg/mL or greater, 150 μg/mL or greater, 200 μg/mL or greater, 250 μg/mL or greater, or 300 μg/mL or greater. In another embodiment, the treatment maintains a serum trough concentration of the anti-C5 antibody or antigen binding fragment thereof of between 100 μg/mL and 200 μg/mL. In another embodiment, the treatment maintains a serum trough concentration of the anti-C5 antibody or antigen binding fragment thereof of about 175 μg/mL.

In another embodiment, to obtain an effective response, the anti-C5 antibody is administered to the patient in an amount and with a frequency to maintain at least 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg, 250 μg, 255 μg or 260 μg of antibody per milliliter of the patient's blood. In another embodiment, the anti-C5 antibody is administered to the patient in an amount and with a frequency to maintain between 50 μg and 250 μg of antibody per milliliter of the patient's blood. In another embodiment, the anti-C5 antibody is administered to the patient in an amount and with a frequency to maintain between 100 μg and 200 μg of antibody per milliliter of the patient's blood. In another embodiment, the anti-C5 antibody is administered to the patient in an amount and with a frequency to maintain about 175 μg of antibody per milliliter of the patient's blood.

In another embodiment, to obtain an effective response, the anti-C5 antibody is administered to the patient in an amount and with a frequency to maintain a minimum free C5 concentration. In one embodiment, for example, the anti-C5 antibody is administered to the patient in an amount and with a frequency to maintain a free C5 concentration of 0.2 μg/mL, 0.3 μg/mL, 0.4 μg/mL, 0.5 μg/mL or less.

The anti-C5 antibodies, or antigen binding fragments thereof, can be administered to a patient by any suitable means. In one embodiment, the antibodies are formulated for intravenous administration.

The efficacy of the treatment methods provided herein can be assessed using any suitable means. In one embodiment, for a pediatric PNH patient, the treatment produces at least one therapeutic effect selected from the group consisting of: a reduction or cessation in fatigue, abdominal pain, dyspnea, dysphagia and chest pain compared to baseline. In another embodiment, the treatment results in terminal complement inhibition. In another embodiment, the treatment results in a reduction of hemolysis as assessed by lactate dehydrogenase (LDH) levels compared to baseline. In another embodiment, the treatment produces a shift toward normal levels of at least one hemolysis-related hematologic biomarker selected, for example, from the group consisting of: free hemoglobin, haptoglobin, reticulocyte count, PNH red blood cell (RBC) clone and D-dimer. In another embodiment, the treatment produces a reduction in the need for blood transfusions compared to baseline. In another embodiment, the treatment produces a reduction in major adverse vascular events (MAVEs). In another embodiment, the treatment produces a shift toward normal levels of a chronic disease associated biomarker selected from the group consisting estimated glomerular filtration rate (eGFR) and spot urine:albumin:creatinine and plasma brain natriuretic peptide (BNP). In another embodiment, the treatment produces a change from baseline in quality of life as assessed via the Functional Assessment of Chronic Illness Therapy (FACIT)-Fatigue Scale, version 4 and the European Organisation for Research and Treatment of Cancer, Quality of Life Questionnaire-Core 30 Scale compared to baseline.

In a particular embodiment, LDH levels are used to evaluate responsiveness to a therapy (e.g., a reduction of hemolysis as assessed by LDH levels is indicative of an improvement in at least one sign of PNH). In one embodiment, patients treated according to the disclosed methods experience reductions in LDH levels to near normal levels or to within 10%, or within 20% above what is considered the normal level (e.g., within 105-333 IU/L (international units per liter). In another embodiment, the patient's LDH levels are normalized throughout maintenance period of treatment. In another embodiment, the treated patient's LDH levels are normalized at least at least 95% of the time while on the maintenance period of treatment. In another embodiment, the treated patient's LDH levels are normalized at least at least 90%, 85% or 80% of the time while on the maintenance period of treatment. In one embodiment, the patient's LDH levels are ≥1.5 fold above the upper limit of normal (LDH≥1.5×ULN) prior to initiating treatment.

In one embodiment, patients treated according to the disclosed methods experience reductions in LDH levels to within normal levels or to within 10%, 20%, 30%, 40% or within 50% below what is considered the ULN level (e.g., within 105-333 IU/L (international units per liter). In one embodiment, the patient's LDH levels are ≥1.5 fold above the ULN (LDH≥1.5×ULN) prior to initiating treatment.

In another aspect, an anti-C5 antibody or antigen binding fragment thereof is provided, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8, for administration: (a) once on Day 1 at a dose of 600 mg to a patient weighing ≥5 to <10 kg, 600 mg to a patient weighing ≥10 to <20 kg, 900 mg to a patient weighing ≥20 to <30 kg, 1200 mg to a patient weighing ≥30 to <40 kg, 2400 mg to a patient weighing ≥40 to <60 kg, 2700 mg to a patient weighing ≥60 to <100 kg, or 3000 mg to a patient weighing ≥100 kg; and (b) on Day 15 and every four weeks thereafter at a dose of 300 mg to a patient weighing ≥5 to <10 kg or 600 mg to a patient weighing ≥10 to <20 kg; or on Day 15 and every eight weeks thereafter at a dose of 2100 mg to a patient weighing ≥20 to <30 kg, 2700 mg to a patient weighing 30 to <40 kg, 3000 mg to a patient weighing 40 to <60 kg, 3300 mg to a patient weighing 60 to <100 kg, or 3600 mg to a patient weighing 100 kg.

In one embodiment, the antibody is determined to be safe, tolerable and sufficiently non-immunogenic after multiple IV doses for use in PNH pediatric patients.

Further provided are kits that include a pharmaceutical composition containing an anti-C5 antibody or antigen binding fragment thereof, such as ravulizumab, and a pharmaceutically acceptable carrier, in a therapeutically effective amount adapted for use in the methods described herein. In one embodiment, the kit comprises: (a) a dose of an anti-C5 antibody or antigen binding fragment thereof, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8; and (b) instructions for using the anti-C5 antibody or antigen binding fragment thereof in the methods described herein.

In one embodiment, 300 mg or 600 mg of the anti-C5 antibody or antigen binding fragment thereof is administered to a patient weighing ≥5 to <10 kg. In another embodiment, 600 mg of the anti-C5 antibody or antigen binding fragment thereof is administered to a patient weighing ≥10 to <20 kg. In another embodiment, 900 mg or 2100 mg of the anti-C5 antibody or antigen binding fragment thereof is administered to a patient weighing ≥20 to <30 kg. In another embodiment, 1200 mg or 2700 mg of the anti-C5 antibody or antigen binding fragment thereof is administered to a patient weighing ≥30 to <40 kg. In another embodiment, 2400 mg or 3000 mg of the anti-C5 antibody or antigen binding fragment thereof is administered to a patient weighing ≥40 to <60 kg. In another embodiment, 2700 mg or 3300 mg of the anti-C5 antibody or antigen binding fragment thereof is administered to a patient weighing ≥60 to <100 kg. In another embodiment, 3000 mg or 3600 mg of the anti-C5 antibody or antigen binding fragment thereof is administered to a patient weighing ≥100 kg.

DETAILED DESCRIPTION

I. Definitions

As used herein, the term "subject" or "patient" is a human patient (e.g., a patient having Paroxysmal Nocturnal Hemoglobinuria (PNH)).

As used herein, the term "pediatric" patient is a human patient under 18 years of age (<18 years of age).

PNH is an acquired hemolytic disorder that occurs most frequently in adults (Brodsky, R., *Blood*, 126:2459-65, 2015). The disease begins with the clonal expansion of a hematopoietic stem cell that has acquired a somatic mutation in the PIGA gene (Brodsky, R., *Blood*, 124:2804-11, 2014). Consequently, PNH blood cells lack the glycophosphatidylinositol (GPI) anchor protein and are deficient in the membrane-bound complement inhibitory proteins CD55 and CD59. In the absence of CD55, there is increased deposition of complement protein C3 cleavage products on blood cell membrane surfaces, in turn leading to cleavage of C5 into C5a and C5b. The pathology and clinical presentations in patients with PNH are driven by uncontrolled terminal complement activation.

C5a is a potent anaphylatoxin, chemotactic factor, and cell-activating molecule that mediates multiple pro-inflammatory and pro-thrombotic activities (Matis, L & Rollins, S., *Nat. Med.*, 1:839-42, 1995; Prodinger et al., Complement. In: Paul W E, editor. Fundamental immunology (4th ed). Philadelphia: Lippincott-Raven Publishers; 1999. p. 967-95). C5b recruits the terminal complement components C6, C7, C8 and C9 to form the pro-inflammatory, pro-thrombotic cytolytic pore molecule C5b-9, a process that under normal circumstances would be blocked on the red blood cell (RBC) membrane by CD59. In patients with PNH, however, these final steps proceed unchecked, culminating in hemolysis and the release of free hemoglobin, as well as platelet activation (Hill, A. et al., *Blood*, 121:4985-96, 2013). The signs and symptoms of PNH can be attributed to chronic, uncontrolled complement C5 cleavage, and release of C5a and C5b-9 leading to RBC hemolysis, which together result in:

release of intracellular free hemoglobin and lactate dehydrogenase (LDH) into circulation as a direct consequence of hemolysis;

irreversible binding to and inactivation of nitric oxide (NO) by hemoglobin, and inhibition of NO synthesis;

vasoconstriction and tissue-bed ischemia due to absence of vasodilatory NO, as well as possible microthrombi manifesting as abdominal pain, dysphagia and erectile dysfunction;

platelet activation; and a pro-inflammatory and prothrombotic state.

A substantial proportion of patients with PNH experience renal dysfunction and pulmonary hypertension (Hillmen, P. et al., *Am. J. Hematol.*, 85:553-9, 2010 [erratum in *Am. J. Hematol.*, 85:911, 2010]; Hill, A. et al., *Br. J. Haematol.*, 158:409-14, 2012). Patients also experience venous or arterial thrombosis in diverse sites, including the abdomen or central nervous system.

In contrast, children with PNH usually present with nonspecific symptoms related to the underlying bone marrow disorder, such as pallor, fatigue or jaundice, with hemoglobinuria appearing less commonly (Ware, R. et al., *N. Engl. J. Med.*, 325:991-6, 1991). Clinical evaluation in pediatric patients also reveals bone marrow failure syndromes, such as, for example, aplastic anemia and refractory cytopenia (van den Heuvel-Eibrink, M., *Paediatr. Drugs*, 9:11-6, 2007). Once the bone marrow disorder is resolved in the child or the PNH clone expands (the cause of which is still unknown), the disease eventually evolves into one more typically seen in adults at presentation.

As used herein, "effective treatment" refers to treatment producing a beneficial effect, e.g., amelioration of at least one symptom of a disease or disorder. A beneficial effect can take the form of an improvement over baseline, e.g., an improvement over a measurement or observation made prior to initiation of therapy according to the method. Effective treatment may refer to alleviation of at least one symptom of PNH (e.g., pallor, fatigue, jaundice, anemia, cytopenia, abdominal pain, dyspnea, dysphagia, chest pain or erectile dysfunction).

The term "effective amount" refers to an amount of an agent that provides the desired biological, therapeutic and/or prophylactic result. That result can be reduction, amelioration, palliation, lessening, delaying and/or alleviation of one or more of the signs, symptoms or causes of a disease, or any other desired alteration of a biological system. In one example, an "effective amount" is the amount of anti-C5 antibody, or antigen binding fragment thereof, clinically proven to alleviate at least one symptom of PNH (e.g., pallor, fatigue, jaundice, anemia, cytopenia, abdominal pain, dyspnea, dysphagia, or chest pain). An effective amount can be administered in one or more administrations.

As used herein, the term "loading dose" refers to the first dose administered (e.g., during an administration cycle).

As used herein, the terms "maintenance" and "maintenance phase" are used interchangeably and refer to the second phase of treatment. In certain embodiments, treatment is continued as long as clinical benefit is observed or until unmanageable toxicity or disease progression occurs.

As used herein, the term "serum trough level" refers to the lowest level that the agent (e.g., the anti-C5 antibody, or antigen binding fragment thereof) or medicine is present in the serum. In contrast, a "peak serum level," refers to the highest level of the agent in the serum. The "average serum level," refers to the mean level of the agent in the serum over time.

The term "antibody" describes a polypeptide comprising at least one antibody-derived antigen binding site (e.g., VH/VL region or Fv, or CDR). Antibodies include known forms of antibodies, e.g., the antibody can be a human antibody, a humanized antibody, a bispecific antibody or a chimeric antibody. The antibody also can be a Fab, Fab'2, ScFv, SMIP, Affibody®, nanobody or a single-domain antibody. The antibody also can be of any of the following isotypes: IgG1, IgG2, IgG3, IgG4, IgM, IgA1, IgA2, IgAsec, IgD, IgE or combinations thereof. The antibody can be a naturally occurring antibody or an antibody that has been altered by a protein engineering technique (e.g., by mutation, deletion, substitution, conjugation to a non-antibody moiety). An antibody can include, for example, one or more variant amino acids (compared to a naturally occurring antibody) that change a property (e.g., a functional property) of the antibody. Numerous such alterations are known in the art that affect, e.g., half-life, effector function, and/or immune responses to the antibody in a patient. The term antibody also includes artificial or engineered polypeptide constructs that comprise at least one antibody-derived antigen binding site.

II. Anti-C5 Antibodies

Anti-C5 antibodies described herein bind to complement component C5 (e.g., human C5) and inhibit the cleavage of C5 into fragments C5a and C5b. As described above, such antibodies also have, for example, improved pharmacokinetic properties relative to other anti-C5 antibodies (e.g., eculizumab) used for therapeutic purposes.

Anti-C5 antibodies (or VH/VL domains derived therefrom) suitable for use in the methods described herein can be generated using methods known in the art. Alternatively, art recognized anti-C5 antibodies can be used. Antibodies that compete for binding to C5 with any of these art recognized antibodies or antibodies described herein can also be used.

An exemplary anti-C5 antibody is ravulizumab comprising heavy and light chains having the sequences shown in SEQ ID NOs:14 and 11, respectively, or antigen binding fragments and variants thereof. Ravulizumab (also known as BNJ441 and ALXN1210) is described in PCT/US2015/019225 and U.S. Pat. No. 9,079,949, the entire teachings of which are hereby incorporated by reference. The terms ravulizumab, BNJ441, and ALXN1210 may be used interchangeably throughout this document, but all refer to the same antibody. Ravulizumab selectively binds to human complement protein C5, inhibiting its cleavage to C5a and C5b during complement activation. This inhibition prevents the release of the proinflammatory mediator C5a and the formation of the cytolytic pore-forming membrane attack complex (MAC) C5b-9 while preserving the proximal or early components of complement activation (e.g., C3 and C3b) essential for the opsonization of microorganisms and clearance of immune complexes.

In other embodiments, the antibody comprises the heavy and light chain CDRs or variable regions of ravulizumab. Accordingly, in one embodiment, the antibody comprises the CDR1, CDR2 and CDR3 domains of the VH region of ravulizumab having the sequence set forth in SEQ ID NO:12, and the CDR1, CDR2 and CDR3 domains of the VL region of ravulizumab having the sequence set forth in SEQ ID NO:8. In another embodiment, the antibody comprises heavy chain CDR1, CDR2 and CDR3 domains having the sequences set forth in SEQ ID NOs:19, 18 and 3, respectively, and light chain CDR1, CDR2 and CDR3 domains having the sequences set forth in SEQ ID NOs:4, 5 and 6, respectively. In another embodiment, the antibody comprises VH and VL regions having the amino acid sequences set forth in SEQ ID NO:12 and SEQ ID NO:8, respectively.

Another exemplary anti-C5 antibody is antibody BNJ421 comprising heavy and light chains having the sequences shown in SEQ ID NOs:20 and 11, respectively, or antigen binding fragments and variants thereof. BNJ421 (also known as ALXN1211) is described in PCT/US2015/019225 and U.S. Pat. No. 9,079,949, the entire teachings of which are hereby incorporated by reference.

In other embodiments, the antibody comprises the heavy and light chain CDRs or variable regions of BNJ421. Accordingly, in one embodiment, the antibody comprises the CDR1, CDR2 and CDR3 domains of the VH region of BNJ421 having the sequence set forth in SEQ ID NO:12, and the CDR1, CDR2 and CDR3 domains of the VL region of BNJ421 having the sequence set forth in SEQ ID NO:8. In another embodiment, the antibody comprises heavy chain CDR1, CDR2 and CDR3 domains having the sequences set forth in SEQ ID NOs:19, 18 and 3, respectively, and light chain CDR1, CDR2 and CDR3 domains having the sequences set forth in SEQ ID NOs:4, 5 and 6, respectively. In another embodiment, the antibody comprises VH and VL regions having the amino acid sequences set forth in SEQ ID NO:12 and SEQ ID NO:8, respectively.

The exact boundaries of CDRs are defined differently according to different methods. In some embodiments, the positions of the CDRs or framework regions within a light or heavy chain variable domain are as defined by Kabat et al. [(1991) "Sequences of Proteins of Immunological Interest." NIH Publication No. 91-3242, U.S. Department of Health and Human Services, Bethesda, MD]. In such cases, the CDRs can be referred to as "Kabat CDRs" (e.g., "Kabat LCDR2" or "Kabat HCDR1"). In some embodiments, the positions of the CDRs of a light or heavy chain variable region are as defined by Chothia et al. (*Nature*, 342:877-83, 1989). Accordingly, these regions can be referred to as "Chothia CDRs" (e.g., "Chothia LCDR2" or "Chothia HCDR3"). In some embodiments, the positions of the CDRs of the light and heavy chain variable regions can be defined by a Kabat-Chothia combined definition. In such embodiments, these regions can be referred to as "combined Kabat-Chothia CDRs." Thomas, C. et al. (*Mol. Immunol.*, 33:1389-401, 1996) exemplifies the identification of CDR boundaries according to Kabat and Chothia numbering schemes.

Another exemplary anti-C5 antibody is the 7086 antibody described in U.S. Pat. Nos. 8,241,628 and 8,883,158. In one embodiment, the antibody comprises the heavy and light chain CDRs or variable regions of the 7086 antibody (see U.S. Pat. Nos. 8,241,628 and 8,883,158). In another embodiment, the antibody, or antigen binding fragment thereof, comprises heavy chain CDR1, CDR2 and CDR3 domains having the sequences set forth in SEQ ID NOs:21, 22 and 23, respectively, and light chain CDR1, CDR2 and CDR3 domains having the sequences set forth in SEQ ID NOs:24, 25 and 26, respectively. In another embodiment, the antibody, or antigen binding fragment thereof, comprises the VH region of the 7086 antibody having the sequence set forth in SEQ ID NO:27, and the VL region of the 7086 antibody having the sequence set forth in SEQ ID NO:28.

Another exemplary anti-C5 antibody is the 8110 antibody also described in U.S. Pat. Nos. 8,241,628 and 8,883,158. In one embodiment, the antibody comprises the heavy and light chain CDRs or variable regions of the 8110 antibody. In another embodiment, the antibody, or antigen binding fragment thereof, comprises heavy chain CDR1, CDR2 and CDR3 domains having the sequences set forth in SEQ ID NOs:29, 30 and 31, respectively, and light chain CDR1, CDR2 and CDR3 domains having the sequences set forth in SEQ ID NOs:32, 33 and 34, respectively. In another embodiment, the antibody comprises the VH region of the 8110 antibody having the sequence set forth in SEQ ID NO:35, and the VL region of the 8110 antibody having the sequence set forth in SEQ ID NO:36.

Another exemplary anti-C5 antibody is the 305LO5 antibody described in US2016/0176954A1. In one embodiment, the antibody comprises the heavy and light chain CDRs or variable regions of the 305LO5 antibody. In another embodiment, the antibody, or antigen binding fragment thereof, comprises heavy chain CDR1, CDR2 and CDR3 domains having the sequences set forth in SEQ ID NOs:37, 38 and 39, respectively, and light chain CDR1, CDR2 and CDR3 domains having the sequences set forth in SEQ ID NOs:40, 41 and 42, respectively. In another embodiment, the antibody comprises the VH region of the 305LO5 antibody having the sequence set forth in SEQ ID NO:43, and the VL region of the 305LO5 antibody having the sequence set forth in SEQ ID NO:44.

Another exemplary anti-C5 antibody is the SKY59 antibody (Fukuzawa, T. et al., *Sci. Rep.*, 7:1080, 2017). In one embodiment, the antibody comprises the heavy and light chain CDRs or variable regions of the SKY59 antibody. In another embodiment, the antibody, or antigen binding fragment thereof, comprises a heavy chain comprising SEQ ID NO:45 and a light chain comprising SEQ ID NO:46.

In some embodiments, an anti-C5 antibody described herein comprises a heavy chain CDR1 comprising, or consisting of, the following amino acid sequence: GHIFSNYWIQ (SEQ ID NO:19). In some embodiments, an anti-C5 antibody described herein comprises a heavy chain CDR2 comprising, or consisting of, the following amino acid sequence: EILPGSGHTEYTENFKD (SEQ ID NO:18). In some embodiments, an anti-C5 antibody described herein comprises a heavy chain variable region comprising the following amino acid sequence:

```
                                    (SEQ ID NO: 12)
QVQLVQSGAE VKKPGASVKV SCKASGHIFS NYWIQWVRQA

PGQGLEWMGE ILPGSGHTEY TENFKDRVTM TRDTSTSTVY

MELSSLRSED TAVYYCARYF FGSSPNWYFD VWGQGTLVTV

SS.
```

In some embodiments, an anti-C5 antibody described herein comprises a light chain variable region comprising the following amino acid sequence:

```
                                    (SEQ ID NO: 8)
DIQMTQSPSS LSASVGDRVT ITCGASENIY GALNWYQQKP

GKAPKLLIYG ATNLADGVPS RFSGSGSGTD FTLTISSLQP

EDFATYYCQN VLNTPLIFGQ GTKVEIK.
```

An anti-C5 antibody described herein can, in some embodiments, comprise a variant human Fc constant region that binds to human neonatal Fc receptor (FcRn) with greater affinity than that of the native human Fc constant region from which the variant human Fc constant region was derived. The Fc constant region can, for example, comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., PCT/US2015/019225 and U.S. Pat. No. 9,079,949 the disclosures of each of which are incorporated herein by reference in their entirety.

Substitutions that enhance the binding affinity of an antibody Fc constant region for FcRn are known in the art and include, e.g., (1) the M252Y/S254T/T256E triple substitution (Dall'Acqua, W. et al., *J. Biol. Chem.*, 281:23514-24, 2006); (2) the M428L or T250Q/M428L substitutions (Hinton, P. et al., *J. Biol. Chem.*, 279:6213-6, 2004; Hinton, P. et al., *J. Immunol.*, 176:346-56, 2006); and (3) the N434A or T307/E380A/N434A substitutions (Petkova, S. et al., *Int. Immunol.*, 18:1759-69, 2006). The additional substitution pairings: P257I/Q311I, P257I/N434H and D376V/N434H (Datta-Mannan, A. et al., *J. Biol. Chem.*, 282:1709-17, 2007), the disclosures of each of which are incorporated herein by reference in their entirety.

In some embodiments, the variant constant region has a substitution at EU amino acid position 255 for valine. In some embodiments, the variant constant region has a substitution at EU amino acid position 309 for asparagine. In some embodiments, the variant constant region has a substitution at EU amino acid position 312 for isoleucine. In some embodiments, the variant constant region has a substitution at EU amino acid position 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, 9, 8, 7, 6, 5, 4, 3 or 2) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I and V308F. In some embodiments, the variant human Fc constant region comprises a methionine at position 428 and an asparagine at position 434 of a native human IgG Fc constant region, each in EU numbering. In some embodiments, the variant Fc constant region comprises a 428L/434S double substitution as described in, e.g., U.S. Pat. No. 8,088,376.

In some embodiments the precise location of these mutations may be shifted from the native human Fc constant region position due to antibody engineering. For example, the 428L/434S double substitution when used in a IgG2/4 chimeric Fc may correspond to 429L and 435S as in the M429L and N435S variants found in ravulizumab and described in U.S. Pat. No. 9,079,949 the disclosure of which is incorporated herein by reference in its entirety.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434 or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312;lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

Suitable anti-C5 antibodies for use in the methods described herein, in some embodiments, comprise a heavy chain polypeptide comprising the amino acid sequence set forth in SEQ ID NO:14 and/or a light chain polypeptide comprising the amino acid sequence set forth in SEQ ID NO:11. Alternatively, the anti-C5 antibodies for use in the methods described herein, in some embodiments, comprise a heavy chain polypeptide comprising the amino acid sequence set forth in SEQ ID NO:20 and/or a light chain polypeptide comprising the amino acid sequence set forth in SEQ ID NO: 11.

In one embodiment, the antibody binds to C5 at pH 7.4 and 25 C (and, otherwise, under physiologic conditions) with an affinity dissociation constant ($K_D$) that is at least 0.1 (e.g., at least 0.15, 0.175, 0.2, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, or 0.975) nM. In some embodiments, the $K_D$ of the anti-C5 antibody, or antigen binding fragment thereof, is no greater than 1 (e.g., no greater than 0.9, 0.8, 0.7, 0.6, 0.5, 0.4, 0.3, or 0.2) nM.

In other embodiments, the [($K_D$ of the antibody for C5 at pH 6.0 at 25 C)/($K_D$ of the antibody for C5 at pH 7.4 at 25 C)] is greater than 21 (e.g., greater than 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1500, 2000, 2500, 3000, 3500, 4000, 4500, 5000, 5500, 6000, 6500, 7000, 7500 or 8000).

Methods for determining whether an antibody binds to a protein antigen and/or the affinity for an antibody to a protein antigen are known in the art. The binding of an antibody to a protein antigen, for example, can be detected and/or quantified using a variety of techniques such as, but not limited to, Western blot, dot blot, surface plasmon resonance (SPR) detection (e.g., BIAcore system; Pharmacia Biosensor AB, Uppsala, Sweden and Piscataway, N.J.), or enzyme-linked immunosorbent assay (ELISA; Benny K. C. Lo (2004) "Antibody Engineering: Methods and Protocols," Humana Press (ISBN: 1588290921); Johne, B. et al., *J. Immunol. Meth.*, 160:191-8, 1993; Jönsson, U. et al., *Ann. Biol. Clin.*, 51:19-26, 1993; Jönsson, U. et al., *Biotechniques*, 11:620-7, 1991). In addition, methods for measuring the affinity (e.g., dissociation and association constants) are set forth in the working examples.

As used herein, the term "$k_a$" refers to the rate constant for association of an antibody to an antigen. The term "$k_d$" refers to the rate constant for dissociation of an antibody from the antibody/antigen complex. And the term "$K_D$" refers to the equilibrium dissociation constant of an antibody-antigen interaction. The equilibrium dissociation constant is deduced from the ratio of the kinetic rate constants, $K_D=k_d/k_a$. Such determinations can be measured, for example, at 25 C or 37 C (see the working examples). The kinetics of antibody binding to human C5 can be determined, for example, at pH 8.0, 7.4, 7.0, 6.5 and 6.0 via SPR on a BIAcore 3000 instrument using an anti-Fc capture method to immobilize the antibody.

In one embodiment, the anti-C5 antibody, or antigen binding fragment thereof, blocks the cleavage of C5 into C5a and C5b. Through this blocking effect, for example, the pro-inflammatory effects of C5a and the generation of the C5b-9 membrane attack complex (MAC) at the surface of a cell are inhibited.

Methods for determining whether a particular antibody described herein inhibits C5 cleavage are known in the art. Inhibition of human complement component C5 can reduce the cell-lysing ability of complement in a subject's body fluids. Such reductions of the cell-lysing ability of complement present in the body fluid(s) can be measured by methods known in the art such as, for example, by a conventional hemolytic assay such as the hemolysis assay (Kabat and Mayer (eds.), "Experimental Immunochemistry, $2^{nd}$ Edition," 135-240, Springfield, IL, CC Thomas (1961), pages 135-139), or a conventional variation of that assay such as the chicken erythrocyte hemolysis method (Hillmen, P. et al., *N. Engl. J. Med.*, 350:552-9, 2004). Methods for determining whether a candidate compound inhibits the cleavage of human C5 into forms C5a and C5b are known in the art (Evans, M. et al., *Mol. Immunol.*, 32:1183-95, 1995). The concentration and/or physiologic activity of C5a and C5b in a body fluid can be measured, for example, by methods known in the art. For C5b, hemolytic assays or assays for soluble C5b-9 as discussed herein can be used. Other assays known in the art can also be used. Using assays of these or other suitable types, candidate agents capable of inhibiting human complement component C5 can be screened.

Immunological techniques such as, but not limited to, ELISA can be used to measure the protein concentration of C5 and/or its split products to determine the ability of an anti-C5 antibody, or antigen binding fragment thereof, to inhibit conversion of C5 into biologically active products. In some embodiments, C5a generation is measured. In some embodiments, C5b-9 neoepitope-specific antibodies are used to detect MAC formation.

Hemolytic assays can be used to determine the inhibitory activity of an anti-C5 antibody, or antigen binding fragment thereof, on complement activation. To determine the effect of an anti-C5 antibody, or antigen binding fragment thereof, on classical complement pathway-mediated hemolysis in a serum test solution in vitro, for example, sheep erythrocytes coated with hemolysin or chicken erythrocytes sensitized with anti-chicken erythrocyte antibody are used as target cells. The percentage of lysis is normalized by considering 100% lysis equal to the lysis occurring in the absence of the inhibitor. In some embodiments, the classical complement pathway is activated by a human IgM antibody, for example, as utilized in the Wieslab® Classical Pathway Complement Kit (Wieslab® COMPL CP310, Euro-Diagnostica, Sweden). Briefly, the test serum is incubated with an anti-C5 antibody, or antigen binding fragment thereof, in the presence of a human IgM antibody. The amount of C5b-9 that is generated is measured by contacting the mixture with an enzyme conjugated anti-C5b-9 antibody and a fluorogenic substrate and measuring the absorbance at the appropriate wavelength. As a control, the test serum is incubated in the absence of the anti-C5 antibody, or antigen binding fragment thereof. In some embodiments, the test serum is a C5-deficient serum reconstituted with a C5 polypeptide.

To determine the effect of an anti-C5 antibody, or antigen binding fragment thereof, on alternative pathway-mediated hemolysis, unsensitized rabbit or guinea pig erythrocytes can be used as the target cells. In some embodiments, the serum test solution is a C5-deficient serum reconstituted with a C5 polypeptide. The percentage of lysis is normalized by considering 100% lysis equal to the lysis occurring in the absence of the inhibitor. In some embodiments, the alternative complement pathway is activated by lipopolysaccharide molecules, for example, as utilized in the Wieslab® Alternative Pathway Complement Kit (Wieslab® COMPL AP330, Euro-Diagnostica, Sweden). Briefly, the test serum is incubated with an anti-C5 antibody, or antigen binding fragment thereof, in the presence of lipopolysaccharide. The amount of C5b-9 that is generated is measured by contacting the mixture with an enzyme conjugated anti-C5b-9 antibody and a fluorogenic substrate and measuring the fluorescence at the appropriate wavelength. As a control, the test serum is incubated in the absence of the anti-C5 antibody, or antigen binding fragment thereof.

In some embodiments, C5 activity, or inhibition thereof, is quantified using a CH50eq assay. The CH50eq assay is a method for measuring the total classical complement activity in serum. This test is a lytic assay, which uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured. The assay is known and commonly practiced by those of skill in the art. Briefly, to activate the classical complement pathway, undiluted serum samples (e.g., reconstituted human serum samples) are added to microassay wells containing the antibody-sensitized erythrocytes to thereby generate TCC. Next, the activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and to each well is added a detection reagent that is detectably labeled and recognizes the bound TCC. The detectable label can be, e.g., a fluorescent label or an enzymatic label. The assay results are expressed in CH50 unit equivalents per milliliter (CH50 U Eq/mL).

Inhibition, e.g., as it pertains to terminal complement activity, includes at least a 5 (e.g., at least a 6, 7, 8, 9, 10, 15, 20, 25, 30, 35, 40, 45, 50, 55 or 60) % decrease in the activity of terminal complement in, e.g., a hemolytic assay or CH50eq assay as compared to the effect of a control antibody (or antigen-binding fragment thereof) under similar conditions and at an equimolar concentration. Substantial inhibition, as used herein, refers to inhibition of a given activity (e.g., terminal complement activity) of at least 40 (e.g., at least 45, 50, 55, 60, 65, 70, 75, 80, 85, 90, or 95 or greater) %. In some embodiments, an anti-C5 antibody described herein contains one or more amino acid substitutions relative to the CDRs of eculizumab (i.e., SEQ ID NOs:1-6), yet retains at least 30 (e.g., at least 31, 32, 33, 34, 35, 36, 37, 38, 39, 40, 41, 42, 43, 44, 45, 46, 47, 48, 49, 50, 55, 60, 65, 70, 75, 80, 85, 90 or 95) % of the complement inhibitory activity of eculizumab in a hemolytic assay or CH50eq assay.

An anti-C5 antibody described herein has a serum half-life in humans that is at least 20 (e.g., at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55) days. In another embodiment, the anti-C5 antibody described herein has a serum half-life in humans that is at least 40 days. In another embodiment, the anti-C5 antibody described herein has a serum half-life in humans that is approximately 43 days. In another embodiment, the anti-C5 antibody described herein has a serum half-life in humans that is between 39-48 days. Methods for measuring the serum half-life of an antibody are known in the art. In some embodiments, an anti-C5 antibody, or antigen binding fragment thereof, described herein has a serum half-life that is at least 20 (e.g., at least 30, 35, 40, 45, 50, 55, 60, 65, 70, 75, 80, 85, 90, 95, 100, 125, 150, 175, 200, 250, 300, 400 or 500) % greater than the serum half-life of eculizumab, e.g., as measured in one of the mouse model systems described in the working examples (e.g., the C5-deficient/NOD/scid mouse or hFcRn transgenic mouse model system).

In one embodiment, the antibody competes for binding with, and/or binds to the same epitope on C5 as an antibody described herein. The term "binds to the same epitope" with reference to two or more antibodies means that the antibodies bind to the same segment of amino acid residues, as determined by a given method. Techniques for determining whether antibodies bind to the same epitope on C5 with an antibody described herein include, for example, epitope mapping methods, such as, x-ray analyses of crystals of antigen:antibody complexes, and hydrogen/deuterium exchange mass spectrometry (HDX-MS). Other methods monitor the binding of the antibody to peptide antigen fragments or mutated variations of the antigen where loss of binding due to a modification of an amino acid residue within the antigen sequence is often considered an indication of an epitope component. In addition, computational combinatorial methods for epitope mapping can also be used.

These methods rely on the ability of the antibody of interest to affinity isolate specific short peptides from combinatorial phage display peptide libraries. Antibodies having the same VH and VL or the same CDR1, CDR2 and CDR3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the antibody that is incubated first with the target). Competing antibodies can bind to, for example, the same epitope, an overlapping epitope or to adjacent epitopes (e.g., as evidenced by steric hindrance).

Anti-C5 antibodies, or antigen-binding fragments thereof described herein, used in the methods described herein can be generated using a variety of art-recognized techniques. Monoclonal antibodies can be obtained by various techniques familiar to those skilled in the art. Briefly, spleen cells from an animal immunized with a desired antigen are immortalized, commonly by fusion with a myeloma cell (Köhler, G. & Milstein, C., *Eur. J. Immunol.,* 6:511-9, 1976)). Methods of immortalization include transformation with Epstein Barr Virus, oncogenes, or retroviruses or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a binding fragment thereof by screening a DNA library from human B cells (Huse, W. et al., *Science,* 246:1275-81, 1989).

III. Compositions

Also provided herein are compositions comprising an anti-C5 antibody or antigen binding fragment thereof. In one embodiment, the composition comprises an anti-C5 antibody comprising the CDR1, CDR2 and CDR3 domains in a heavy chain variable region having the sequence set forth in SEQ ID NO:12, and the CDR1, CDR2 and CDR3 domains in a light chain variable region having the sequence set forth in SEQ ID NO:8. In another embodiment, the anti-C5 antibody comprises heavy and light chains having the sequences shown in SEQ ID NOs:14 and 11, respectively. In another embodiment, the anti-C5 antibody comprises heavy and light chains having the sequences shown in SEQ ID NOs:20 and 11, respectively.

The compositions can be formulated as a pharmaceutical solution, e.g., for administration to a subject for the treatment or prevention of a complement-associated disorder. The pharmaceutical compositions generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt, sugars, carbohydrates, polyols and/or tonicity modifiers.

The compositions can be formulated according to standard methods. Pharmaceutical formulation is an established art (see, for example, Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X)). In some embodiments, a composition can be formulated, for example, as a buffered solution at a suitable concentration and suitable for storage at 2-8 C (e.g., 4 C). In some embodiments, a composition can be formulated for storage at a temperature below OC (e.g., −20 C or −80 C). In some embodiments, the composition can be formulated for storage for up to 2 years (e.g., 1 month, 2 months, 3 months, 4 months, 5 months, 6 months, 7 months, 8 months, 9 months, 10 months, 11 months, 1 year, 1½ years or 2 years) at 2-8 C (e.g., 4 C). Thus, in some embodiments, the compositions described herein are stable in storage for at least 1 year at 2-8 C (e.g., 4 C).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. Compositions containing a composition intended for systemic or local delivery, for example, can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally" and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

IV. Outcomes

Provided herein are methods for treating PNH in a patient comprising administering to the patient an anti-C5 antibody. Symptoms of PNH include, but are not limited to, pallor, fatigue (e.g., tiredness, difficultly performing daily activities, trouble concentrating, dizziness, weakness), pain (e.g., stomach pain, leg pain or swelling, chest pain, back pain), dark-colored urine, shortness of breath, difficulty swallowing, yellowing of the skin and/or eyes, anemia, cytopenia, erectile dysfunction, blood clots, kidney disease, damage to organs, stroke or heart attack.

Patients treated according to the methods disclosed herein experience improvement in at least one sign of PNH. The treatment may produce at least one therapeutic effect selected from the group consisting of, for example, a reduction or cessation in pallor, fatigue, jaundice, anemia, cytopenia, abdominal pain, dyspnea, dysphagia, chest pain or erectile dysfunction.

In one embodiment, improvement is measured by terminal complement inhibition.

In another embodiment, lactate dehydrogenase (LDH) levels can be used to evaluate responsiveness to a therapy (e.g., a reduction of hemolysis as assessed by lactate dehydrogenase (LDH) levels is indicative of an improvement in at least one sign of PNH). LDH is a marker of intravascular hemolysis (Hill, A. et al., *Br. J. Haematol.*, 149:414-25, 2010; Hillmen, P. et al., *N. Engl. J. Med.*, 350:552-9, 2004; Parker, C. et al., *Blood*, 106:3699-709, 2005). Red blood cells contain large amounts of LDH, and a correlation between cell-free hemoglobin and LDH concentration has been reported in vitro (Van Lente, F. et al., *Clin. Chem.*, 27:1453-5, 1981) and in vivo (Kato, G. et al., *Blood*, 107:2279-85, 2006). The consequences of hemolysis are independent of anemia (Hill, A. et al., *Haematologica*, 93(s1):359Abs.0903, 2008; Kanakura, Y et al., *Int. J. Hematol.*, 93:36-46, 2011). LDH concentration obtained at baseline and then serially throughout a treatment period, is an important measure of hemolysis. Baseline levels of cell-free plasma hemoglobin are highly elevated in patients with PNH with LDH≥1.5-fold above the upper limit of normal (LDH≥1.5×ULN), with a significant correlation between LDH and cell-free plasma hemoglobin (Hillmen, P. et al., *N. Engl. J. Med.*, 355:1233-43, 2006). The normal LDH value range is 105-333 IU/L (international units per liter).

LDH levels can be measured using any suitable test or assay, such as those described by Ferri F F, ed. *Ferri's Clinical Advisor* 2014. Philadelphia: Pa: Elsevier Mosby; 2014: Section IV—Laboratory tests and interpretation of results. LDH concentration can be measured in various samples obtained from a patient, in particular, serum samples. As used herein, the term "sample" refers to biological material from a subject. Although serum LDH concentration is of interest, samples can be derived from other sources, including, for example, single cells, multiple cells, tissues, tumors, biological fluids, biological molecules or supernatants or extracts of any of the foregoing. Examples include tissue removed for biopsy, tissue removed during resection, blood, urine, lymph tissue, lymph fluid, cerebrospinal fluid, mucous and stool samples. The sample used can vary based on the assay format, the detection method and the nature of the tumors, tissues, cells or extracts to be assayed. Methods for preparing samples are known in the art and can be readily adapted to obtain a sample that is compatible with the method utilized.

In one embodiment, patients treated according to the disclosed methods experience reductions in LDH levels to normal levels or to within 10%, or within 20% above what is considered the normal level (e.g., within 105-333 IU/L). In one embodiment, the patient's LDH levels are ≥1.5 fold above the upper limit of normal (LDH≥1.5×ULN) prior to initiating treatment.

In another embodiment, the treatment produces a shift toward normal levels of a hemolysis-related hematologic biomarker selected from the group consisting of free hemoglobin, haptoglobin, reticulocyte count, PNH red blood cell (RBC) clone and D-dimer.

In another embodiment, the treatment produces a reduction in the need for blood transfusions compared to baseline.

In another embodiment, the treatment produces a reduction in major adverse vascular events (MAVEs; e.g., thrombophlebitis/deep vein thrombosis, pulmonary embolus, myocardial infarction, transient ischemic attack, unstable angina, renal vein thrombosis/renal artery thrombosis/glomerular thrombosis, renal infarction, acute peripheral vascular occlusion, mesenteric/visceral vein/arterial thrombosis or infarction, hepatic/portal vein thrombosis, cerebral arterial occlusion/cerebrovascular accident, cerebral venous occlusion, renal arterial thrombosis, or multi-infarct dementia).

In another embodiment, the treatment produces a shift toward normal levels of a chronic disease associated biomarker selected from the group consisting estimated glomerular filtration rate (eGFR) and spot urine:albumin:creatinine and plasma brain natriuretic peptide (BNP).

In another embodiment, the treatment produces a change from baseline in quality of life as assessed via the Functional Assessment of Chronic Illness Therapy (FACIT)-Fatigue Scale, version 4 and the European Organisation for Research and Treatment of Cancer, Quality of Life Questionnaire-Core 30 Scale compared to baseline.

V. Kits and Unit Dosage Forms

Also provided herein are kits that include a pharmaceutical composition containing an anti-C5 antibody or antigen binding fragment thereof, such as ravulizumab or BNJ421, and a pharmaceutically acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having PNH. The kit also can include a syringe.

Optionally, the kits include multiple packages of the single-dose pharmaceutical compositions each containing an effective amount of the anti-C5 antibody, or antigen binding fragment thereof, for a single administration in accordance with the methods provided above. Instruments or devices necessary for administering the pharmaceutical composition(s) also may be included in the kits. For instance, a kit may provide one or more pre-filled syringes containing an amount of the anti-C5 antibody or antigen binding fragment thereof.

In one embodiment, a kit for treating PNH in a human pediatric patient comprises: (a) a dose of an anti-C5 antibody or antigen binding fragment thereof, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8; and (b) instructions for using the anti-C5 antibody or antigen binding fragment thereof, according to any of the methods described herein.

In one embodiment, the kit comprises a dose of an anti-C5 antibody or antigen binding fragment thereof, wherein the anti-C5 antibody or antigen binding fragment thereof, is administered to a patient weighing ≥5 to <10 kg: (a) once on Day 1 at a dose of 600 mg; and (b) on Day 15 and every four weeks thereafter at a dose of 300 mg.

In another embodiment, the kit comprises a dose of an anti-C5 antibody or antigen binding fragment thereof, wherein the anti-C5 antibody or antigen binding fragment thereof, is administered to a patient weighing ≥10 to <20 kg: (a) once on Day 1 at a dose of 600 mg; and (b) on Day 15 and every four weeks thereafter at a dose of 600 mg.

In another embodiment, the kit comprises a dose of an anti-C5 antibody or antigen binding fragment thereof, wherein the anti-C5 antibody, or antigen binding fragment thereof, is administered to a patient weighing 20 to <30 kg: (a) once on Day 1 at a dose of 900 mg; and (b) on Day 15 and every eight weeks thereafter at a dose of 2100 mg.

In another embodiment, the kit comprises a dose of an anti-C5 antibody or antigen binding fragment thereof, wherein the anti-C5 antibody, or antigen binding fragment thereof, is administered to a patient weighing 30 to <40 kg: (a) once on Day 1 at a dose of 1200 mg; and (b) on Day 15 and every eight weeks thereafter at a dose of 2700 mg.

In another embodiment, the kit comprises a dose of an anti-C5 antibody, or antigen binding fragment thereof, wherein the anti-C5 antibody, or antigen binding fragment thereof, is administered to a patient weighing 40 to <60 kg: (a) once on Day 1 at a dose of 2400 mg; and (b) on Day 15 and every eight weeks thereafter at a dose of 3000 mg.

In another embodiment, the kit comprises a dose of an anti-C5 antibody or antigen binding fragment thereof, wherein the anti-C5 antibody, or antigen binding fragment thereof, is administered to a patient weighing 60 to <100 kg: (a) once on Day 1 at a dose of 2700 mg; and (b) on Day 15 and every eight weeks thereafter at a dose of 3300 mg. In another embodiment, the kit comprises a dose of an anti-C5 antibody or antigen binding fragment thereof, wherein the anti-C5 antibody, or antigen binding fragment thereof, is administered to a patient weighing 100 kg: (a) once on Day 1 at a dose of 3000 mg; and (b) on Day 15 and every eight weeks thereafter at a dose of 3600 mg.

The following examples are merely illustrative and should not be construed as limiting the scope of this disclosure in any way as many variations and equivalents will become apparent to those skilled in the art upon reading the present disclosure. The contents of all references, Genbank entries, patents and published patent applications cited throughout this application are expressly incorporated herein by reference.

EXAMPLES

Example 1: A Phase 3, Open-Label Study of Ravulizumab in Children and Adolescents with Paroxysmal Nocturnal Hemoglobinuria (PNH)

In this Phase 3, open-label study, the pharmacokinetic(s) (PK), pharmacodynamics (PD), efficacy, and safety of ravulizumab are assessed in pediatric patients with PNH.

1. Objectives

The primary objective of the study is to assess the PK, PD, safety and efficacy of ravulizimab in pediatric patients with PNH.

2. Endpoints

The primary endpoints are PK/PD parameters (trough and peak) at Baseline and Weeks 2, 10, 18, and 26. PK parameters include maximum serum concentration ($C_{max}$), trough serum concentration (measured at end of dosing interval at steady state; $C_{trough}$), and accumulation ratio. PD parameters include measuring the change in free C5 concentrations and in chicken red blood cell (cRBC) hemolytic activity over time.

Secondary endpoints include assessment of the following parameters:

Percentage change in LDH from baseline to Day 183 (Week 26);

Transfusion avoidance (TA), defined as the proportion of patients who remain transfusion-free and do not require a transfusion through Day 183 (Week 26);

Change in quality of life (QoL), as measured by Pediatric Functional Assessment of Chronic Therapy (FACIT) Fatigue questionnaire (patients ≥5 years of age), from baseline to Day 183 (Week 26);

Proportion of patients with stabilized hemoglobin, defined as avoidance of a ≥2 g/dL decrease in hemoglobin level from baseline in the absence of transfusion through Day 183 (Week 26);

Percentage change in free hemoglobin from baseline to Day 183 (Week 26);

Proportion of patients with breakthrough hemolysis, defined as at least one new or worsening symptom or sign of intravascular hemolysis (fatigue, hemoglobinuria, abdominal pain, shortness of breath [dyspnea], anemia, major adverse vascular event [MAVE, including thrombosis], dysphagia, or erectile dysfunction) in the presence of elevated LDH as follows: for patients who enter the study naïve to complement inhibitor treatment, elevated LDH≥2×the upper limit of normal (ULN) after prior LDH reduction to <1.5×ULN on therapy; for patients who enter the study stabilized on eculizumab treatment, elevated LDH≥2×ULN.

With respect to safety endpoints, the safety and tolerability of ravulizumab is evaluated from baseline to Week 26 and throughout the extension period by physical examinations, vital signs, physical growth (height, weight, and head circumference [the latter only in patients who are ≤3 years of age]), electrocardiograms (ECGs), laboratory assessments, and incidence of adverse events (AEs) and serious adverse events (SAEs). The proportion of patients who develop antidrug antibodies (ADAs) is also assessed.

3. Study Design

This is a Phase 3, open-label, single-arm multicenter study to evaluate the PK/PD, safety, and efficacy of ravulizumab administered by intravenous (IV) infusion to pediatric patients (<18 years of age) with PNH. The study consists of a 4-week Screening Period, a 26-week Primary Evaluation Period and an Extension Period.

Consenting patients are screened for study eligibility up to 4 weeks prior to Day 1. Patients who satisfy all of the inclusion criteria and all of the exclusion criteria are enrolled into the Primary Evaluation Period and receive a weight-based loading dose of ravulizumab on Day 1, followed by weight-based maintenance treatment with ravulizumab on Day 15 and once every 8 weeks (q8w) thereafter for patients weighing ≥20 kg, or once every 4 weeks (q4w) for patients weighing <20 kg, for a total of 26 weeks of treatment. For patients entering the study on eculizumab therapy, Day 1 of study treatment occurs 2 weeks from the patient's last dose of eculizumab.

An interim analysis of data, including ravulizumab PK and free C5 levels, is conducted after 4 patients weighing ≥5 kg to <40 kg have completed dosing through Day 71. Enrollment of patients proceeds without interruption while the analysis is ongoing. The accrued safety and PK/PD data is assessed to ensure that ravulizumab treatment is well tolerated and is providing adequate complement inhibition. In addition, an independent Data Monitoring Committee (DMC) reviews safety data from the study on a regular basis.

After completion of all assessments on Day 183, all patients enter an Extension Period and continue to receive ravulizumab according to the appropriate weight-based regimen. The Extension Period continues until the product is registered or approved (in accordance with country-specific regulations) or for up to 2 years, whichever occurs first. The end of trial is defined as the last patient's last visit in the Extension Period.

4. Schedule of Assessments

The Schedule of Assessments is set forth in Table 1 for the Screening and Primary Evaluation Period and in Table 2 for the Extension Period.

Additional (unscheduled) visits outside the specified visits are permitted at the discretion of the Investigator. Procedures, tests, and assessments are performed at the discretion of the Investigator. All tests, procedures, or assessments performed at the Unscheduled Visits are recorded on the electronic case report forms (eCRFs).

Additionally, if a suspected event of breakthrough hemolysis occurs, LDH, PK and PD parameters are analyzed at the central laboratory. If the suspected event of breakthrough does not occur at a scheduled visit, an unscheduled visit occurs for evaluation of the patient and collection of the required LDH, PK and PD parameters. For purposes of defining breakthrough hemolysis, assessment of LDH is based on a central laboratory value.

TABLE 1

Schedule of Study Visits and Assessments: Screening Through End of Primary Evaluation Period

| | Period | | | | | | | |
|---|---|---|---|---|---|---|---|---|
| | Screening | Initial Evaluation Period Study Day | | | | | | |
| | −28 to −1 | 1 | 15 | 43 | 71 | 99 | 127 | 155 | 183[a]/ET |
| | | | | | Window (day) | | | | |
| | N/A | | ±3 | ±3 | ±3 | ±5 | ±5 | ±5 | ±2 |
| Informed consent | X | | | | | | | | |
| Confirmation or administration of meningococcal vaccination[b] | X | X | | | | | | | |
| Confirmation of H influenza type B and S pneumoniae vaccination (per local/national guidelines) | X | | | | | | | | |
| Medical history and demographics | X | | | | | | | | |
| PNH clone size[c] | X | X | | | X | | | | X |
| Head circumference (patients ≤ 3 years of age only) | X | X | X | X | X | X | X | X | X |
| Height and weight[d] | X | X | X | X | X | X | X | X | X |
| Pregnancy test[e] | X | X | X | | X | | X | | X |
| Record transfusions (during and between visits) | X | X | X | X | X | X | X | X | X |
| PNH symptomatology[f] | X | X | X | X | X | X | X | X | X |
| Pediatric FACIT-Fatigue questionnaire[g] | | X | X | | X | | X | | X |
| Physical examination | X | | | | | | | | X |
| Abbreviated physical examination[h] | | X | X | X | X | X | X | X | |
| Vital signs[i] | X | X | X | X | X | X | X | X | X |
| Safety 12-Lead ECG[j] | X | | | | X | | | | X |
| Chemistry including LDH[k] | X | X | X | X | X | X | X | X | X |
| Hematology including free hemoglobin and coagulation[k] | X | X | X | X | X | X | X | X | X |
| Urinalysis and urine chemistry[k] | X | X | X | | X | | X | | X |
| PK/PD sampling[m] | | X | X | | X | | X | | X |
| Immunogenicity (ADA)[n] | | X | | | X | | X | | X |
| Review safety card[o] | | X | X | X | X | X | X | X | X |
| Breakthrough hemolysis[p] | | | ←Monitor continuously→ | | | | | | |
| Concomitant medications | X | | ←Monitor continuously→ | | | | | | |
| Adverse events | X | | ←Monitor continuously→ | | | | | | |
| ravulizumab administration (patients weighing < 20 kg)[q, r] | | X[s] | X | X | X | X | X | X | |

TABLE 1-continued

Schedule of Study Visits and Assessments: Screening Through End of Primary Evaluation Period

| | Period | | | | | | | |
|---|---|---|---|---|---|---|---|---|
| | Screening | Initial Evaluation Period Study Day | | | | | | |
| | −28 to −1 | 1 | 15 | 43 | 71 | 99 | 127 | 155 | 183[a]/ET |
| | | | | | Window (day) | | | |
| | N/A | ±3 | ±3 | ±3 | ±5 | ±5 | ±5 | ±2 |
| ravulizumab administration (patients weighing ≥ 20 kg)[q] | | X[s] | X | | X | | X | |

Abbreviations:
ADA = antidrug antibody;
ECG = electrocardiogram;
eCRF = electronic case report form;
EOI = end of infusion;
ET = early termination;
FACIT-Fatigue = Functional Assessment of Chronic Illness Therapy-Fatigue Scale;
LDH = lactate dehydrogenase;
N/A = not applicable;
PD = pharmacodynamics;
PK = pharmacokinetics;
PNH = paroxysmal nocturnal hemoglobinuria;
RBC = red blood cell;
WBC = white blood cell

[a]The primary endpoint assessment is before dosing on Day 183. Dosing on Day 183 is the start of the Extension Period. Please refer to additional Day 183 post-dose assessments in Table 2.
[b]All patients are vaccinated against meningococcal infections within 3 years prior to, or at the time of, initiating study drug. Patients who initiate study drug treatment less than 2 weeks after receiving a meningococcal vaccine receive treatment with appropriate prophylactic antibiotics until 2 weeks after vaccination. Patients who have not been vaccinated prior to initiating ravulizumab treatment receive prophylactic antibiotics prior to and for at least 2 weeks after meningococcal vaccination. Patients who cannot be vacceinated receive antibiotic prophylaxis for the entire treatment period and for 8 months following last dose.
[c]WBC (granulocyte and monocyte) and RBC clone size measured by high-sensitivity flow cytometry at Screening and Day 1; RBC clone size only on Day 71 and Day 183.
[d]Height at baseline and Day 183 only. Weight is collected pre-dose on dosing days.
[e]Pregnancy testing is required only for female patients of childbearing potential (i.e., have achieved menarche). Serum pregnancy test is performed at Screening and Day 183, urine pregnancy test at all other required time points. A negative pregnancy test result is required prior to administering study drug to female patients of childbearing potential at the indicated study visits.
[f]Investigator or designee assessment of the following events: fatigue, hemoglobinuria abdominal pain, dyspnea, dysphagia, chest pain, and erectile dysfunction. On dosing days, assessments are performed prior to dosing.
[g]On dosing days, assessments are performed prior to dosing. Pediatric FACIT-Fatigue only in patients ≥5 years of age (self-reported by patients who were ≥8 years of age at the time of enrollment and reported by caregivers for patients who were ≥5 to <8 years of age at the time of enrollment).
[h]Abbreviated physical examination consists of a body system relevant examination based upon Investigator (or qualified designee) judgment and patient symptoms. At least one body system is checked for an abbreviated exam.
[i]Vital sign measurements are taken after the patient has been resting for at least 5 minutes and include systolic and diastolic blood pressure (BP) (millimeters of mercury [mmHg]), heart rate (beats/minute), respiratory rate (breaths/minute), and temperature (degrees Celsius [C.] or degrees Fahrenheit [° F.]). On dosing days, vital signs are taken pre-dose.
[j]Single 12-lead ECG is collected at Screening and pre-dose on Day 71 and Day 183. Patients are supine for approximately 5 to 10 minutes before ECG collection and remain supine (but awake) during ECG collection.
[k]Clinical laboratory measurements are collected pre-dose on dosing days and not from a heparinized line.
[l]For patients entering the study on eculizumab therapy, screening LDH is obtained within 24 hours prior to a scheduled eculizumab dose.
[m]Serum samples for PK/PD analyses are collected at the indicated visits. For indicated visits falling on dosing days, samples are collected pre-dose (within 0.5 hours prior to the start of infusion) and at end of infusion (EOI) (within 0.5 hours after the EQI from the patient's opposite, noninfused arm). To minimize needle sticks to the patient, the pre-dose sample is drawn through the venous access created for the dose infusion, prior to administration of the dose. As noted, the post-dose sample is drawn from the opposite, non-infused arm. For indicated visits not falling on dosing days, samples are collected at any time that visit day. If a supplemental dose is administered PK/PD samples are collected at pre-dose and at end of infusion. If a loading dose is administered as two separate infusions <24 hours apart, PK/PD samples are collected before the first infusion (i.e., the pre-dose sample) and after the second infusion (i.e., the end of infusion sample). All collection times are recorded in the eCRF.
[n]ADA serum samples are collected pre-dose on Days 1, 71 and 127 or at any time during an ET visit. Day 183 collection occurs prior to first dose in the Extension Period.
[o]Review the Clinical Trial Participant Safety Information Card with the patient/caregiver and discuss the importance of carrying the safety card at all times, and the risks ravulizumab treatment, including the risk of meningococcal infection.
[p]If a suspected event of breakthrough hemolysis occurs, LDH, PK and PD parameters are to be analyzed at the central laboratory. If the suspected event of breakthrough does not occur at a scheduled visit, an unscheduled visit occurs for evaluation of the patient and collection of the required LDH, PK and PD parameters.
[q]Dose regimen is based on body weight obtained at the study visit. If the study drug is prepared the night prior to the visit, the weight from the previous visit is used.
[r]Should a patient's weight change from <20 kg to ≥20 kg on a "q4w only" visit, the patient receives the q4w dose that day. At the patient's next q8w visit, the new q8w dose is given.
[s]For patients entering the study on eculizumab therapy, Day 1 occurs 2 weeks from the patient's last dose of eculizumab Abbreviations: ADA=antidrug antibody; ECG=electrocardiogram; eCRF=electronic case report form; EOI=end of infusion; ET=early termination; FACIT-Fatigue=Functional Assessment of Chronic Illness Therapy-Fatigue Scale; LDH=lactate dehydrogenase; N/A=not applicable; PD=pharmacodynamics; PK=pharmacokinetics; PNH=paroxysmal nocturnal hemoglobinuria; RBC=red blood cell; WBC=white blood cell

[a] The primary endpoint assessment is before dosing on Day 183. Dosing on Day 183 is the start of the Extension Period. Please refer to additional Day 183 post-dose assessments in Table 2.

[b] All patients are vaccinated against meningococcal infections within 3 years prior to, or at the time of, initiating study drug. Patients who initiate study drug treatment less than 2 weeks after receiving a meningococcal vaccine receive treatment with appropriate prophylactic antibiotics until 2 weeks after vaccination. Patients who have not been vaccinated prior to initiating ravulizumab treatment receive prophylactic antibiotics prior to and for at least 2 weeks after meningococcal vaccination. Patients who cannot be vaccinated receive antibiotic prophylaxis for the entire treatment period and for 8 months following last dose.

[c] WBC (granulocyte and monocyte) and RBC clone size measured by high-sensitivity flow cytometry at Screening and Day 1; RBC clone size only on Day 71 and Day 183.

[d] Height at baseline and Day 183 only. Weight is collected pre-dose on dosing days.

[e] Pregnancy testing is required only for female patients of childbearing potential (i.e., have achieved menarche). Serum pregnancy test is performed at Screening and Day 183, urine pregnancy test at all other required time points. A negative pregnancy test result is required prior to administering study drug to female patients of childbearing potential at the indicated study visits.

[f] Investigator or designee assessment of the following events: fatigue, hemoglobinuria abdominal pain, dyspnea, dysphagia, chest pain, and erectile dysfunction. On dosing days, assessments are performed prior to dosing.

[g] On dosing days, assessments are performed prior to dosing. Pediatric FACIT-Fatigue only in patients ≥5 years of age (self-reported by patients who were ≥8 years of age at the time of enrollment and reported by caregivers for patients who were ≥5 to <8 years of age at the time of enrollment).

[h] Abbreviated physical examination consists of a body system relevant examination based upon Investigator (or qualified designee) judgment and patient symptoms. At least one body system is checked for an abbreviated exam.

[i] Vital sign measurements are taken after the patient has been resting for at least 5 minutes and include systolic and diastolic blood pressure (BP) (millimeters of mercury [mmHg]), heart rate (beats/minute), respiratory rate (breaths/minute), and temperature (degrees Celsius [C] or degrees Fahrenheit [° F.]). On dosing days, vital signs are taken pre-dose.

[j] Single 12-lead ECG is collected at Screening and pre-dose on Day 71 and Day 183. Patients are supine for approximately 5 to 10 minutes before ECG collection and remain supine (but awake) during ECG collection.

[k] Clinical laboratory measurements are collected pre-dose on dosing days and not from a heparinized line.

[l] For patients entering the study on eculizumab therapy, screening LDH is obtained within 24 hours prior to a scheduled eculizumab dose.

[m] Serum samples for PK/PD analyses are collected at the indicated visits. For indicated visits falling on dosing days, samples are collected pre-dose (within 0.5 hours prior to the start of infusion) and at end of infusion (EOI) (within 0.5 hours after the EOI from the patient's opposite, noninfused arm). To minimize needle sticks to the patient, the pre-dose sample is drawn through the venous access created for the dose infusion, prior to administration of the dose. As noted, the post-dose sample is drawn from the opposite, non-infused arm. For indicated visits not falling on dosing days, samples are collected at any time during that visit day. If a supplemental dose is administered PK/PD samples are collected at pre-dose and at end of infusion. If a loading dose is administered as two separate infusions <24 hours apart, PK/PD samples are collected before the first infusion (i.e., the pre-dose sample) and after the second infusion (i.e., the end of infusion sample). All collection times are recorded in the eCRF.

[n] ADA serum samples are collected pre-dose on Days 1, 71 and 127 or at any time during an ET visit. Day 183 collection occurs prior to first dose in the Extension Period.

[o] Review the Clinical Trial Participant Safety Information Card with the patient/caregiver and discuss the importance of carrying the safety card at all times, and the risks ravulizumab treatment, including the risk of meningococcal infection.

[p] If a suspected event of breakthrough hemolysis occurs, LDH, PK and PD parameters are to be analyzed at the central laboratory. If the suspected event of breakthrough does not occur at a scheduled visit, an unscheduled visit occurs for evaluation of the patient and collection of the required LDH, PK and PD parameters.

[q] Dose regimen is based on body weight obtained at the study visit. If the study drug is prepared the night prior to the visit, the weight from the previous visit is used.

[r] Should a patient's weight change from <c 20 kg to ≥20 kg on a "q4w only" visit, the patient receives the q4w dose that day. At the patient's next q8w visit, the new q8w dose is given.

[s] For patients entering the study on eculizumab therapy, Day 1 occurs 2 weeks from the patient's last dose of eculizumab

TABLE 2

Schedule of Study Visits and Assessments: Extension Period

| | 183[a] | 211 q4w | 239 | 267 q4w | 295 | 323 q4w | 351 | 379 q4w | 407 | 435 q4w | 463 | 491 q4w | 519 | 547 q4w |
|---|---|---|---|---|---|---|---|---|---|---|---|---|---|---|
| Window (day) | ±2 | ±5 | ±5 | ±5 | ±5 | ±5 | ±5 | ±5 | ±5 | ±5 | ±5 | ±5 | ±5 | ±5 |
| PNH clone size[b] | | | | | | | X | | | | | | | |
| Head circumference (patients ≤ 3 years of age) | | X | | X | | X | | | | X | | X | | X |
| Height and weight[c] | X | X | X | X | X | X | X | X | X | X | X | X | X | X |
| Pregnancy test[d] | | X | | X | | X | | | | | | | | |
| Record transfusions | | X | | X | | X | | | | | | | | |
| PNH symptomatology[e] | | X | | X | | X | | | | | | | | |
| Pediatric FACIT-Fatigue questionnaire[f] | | | | | | | X | | | | | | | |
| Physical examination | | | | | | | | | | | | | | |
| Abbreviated physical examination[g] | | X | | X | | X | | | | | | | | |

TABLE 2-continued

Schedule of Study Visits and Assessments: Extension Period

| | C1 | C2 | C3 | C4 | C5 | C6 | C7 | C8 | C9 | C10 | C11 | C12 | C13 | C14 |
|---|---|---|---|---|---|---|---|---|---|---|---|---|---|---|
| Vital signs[h] | | | X | X | X | | | | | | | | | |
| Safety 12-Lead ECG[i] | | | | | | | | | | | | | | |
| Chemistry including LDH[j] | | | X | X | X | | | | | | | | | |
| Hematology including free hemoglobin and coagulation[j] | | | X | X | X | | | | | | | | | |
| Urinalysis and urine chemistry[j] | | | X | X | X | | | | | | | | | |
| PK/PD sampling[k] | X | | | | | X | | | | | | | | |
| Immunogenicity (ADA)[l] | | | | | | X | | | | | | | | |
| Review safety card[m] | X | X | X | X | X | X | X | X | X | X | X | X | X | X |
| Breakthrough hemolysis[n] | | | | ←Monitor continuously→ | | | | | | | | | | |
| Concomitant medications | | | | ←Monitor continuously→ | | | | | | | | | | |
| Adverse events | | | | ←Monitor continuously→ | | | | | | | | | | |
| ravulizumab administration (patients weighing <20 kg)[o,p] | X[a] | X | X | X | X | X | X | X | X | X | X | X | X | X |
| ravulizumab administration (patients weighing ≥20 kg)[o] | X[a] | | X | | X | | X | | X | | X | | X | |

| | Study Day | | | | | | | | | | | | |
|---|---|---|---|---|---|---|---|---|---|---|---|---|---|
| | 575 | 603 q4w | 631 | 659 q4w | 687 | 715 q4w | 743 | 771 q4w | 799 | 827 q4w | 855 | 883 q4w | 911/ET/EOS |
| | Window (day) | | | | | | | | | | | | |
| | ±5 | ±5 | ±5 | ±5 | ±5 | ±5 | ±5 | ±5 | ±5 | ±5 | ±5 | ±5 | ±5 |
| PNH clone size[b] | X | | | | | | | | | | | | X |
| Head circumference (patients ≤ 3 years of age) | X | | X | | X | | X | | X | | X | | X |
| Height and weight[c] | X | X | X | X | X | X | X | X | X | X | X | X | X |
| Pregnancy test[d] | X | | | | | | X | | | | | | X |
| Record transfusions | X | | | | | | X | | | | | | X |
| PNH symptomatology[e] | X | | | | | | X | | | | | | X |
| Pediatric FACIT-Fatigue questionnaire[f] | X | | | | | | X | | | | | | X |
| Physical examination | | | | | | | | | | | | | X |
| Abbreviated physical examination[g] | X | | | | | | X | | | | | | |
| Vital signs[h] | X | | | | | | X | | | | | | X |
| Safety 12-Lead ECG[i] | | | | | | | | | | | | | |
| Chemistry including LDH[j] | X | | | | | | X | | | | | | X |
| Hematology including | X | | | | | | X | | | | | | X |

TABLE 2-continued

Schedule of Study Visits and Assessments: Extension Period

| Assessment | | | | | | | | | | | | | |
|---|---|---|---|---|---|---|---|---|---|---|---|---|---|
| free hemoglobin and coagulation[j] | | | | | | | | | | | | | |
| Urinalysis and urine chemistry[j] | X | | | | | | X | | | | | | X |
| PK/PD sampling[k] | X | | | | | | X | | | | | | X |
| Immunogenicity (ADA)[l] | | | | | | | X | | | | | | |
| Review safety card[m] | X | X | X | X | X | X | X | X | X | X | X | X | X |
| Breakthrough hemolysis[n] | | | | | | ←Monitor continuously→ | | | | | | | |
| Concomitant medications | | | | | | ←Monitor continuously→ | | | | | | | |
| Adverse events | | | | | | ←Monitor continuously→ | | | | | | | |
| ravulizumab administration (patients weighing <20 kg)[o,p] | X | X | X | X | X | X | X | X | X | X | X | X | |
| ravulizumab administration (patients weighing ≥20 kg)[o] | X | | X | | X | | X | | X | | X | | X |

Abbreviations:
ADA = antidrug antibody;
ECG = electrocardiogram;
eCRF = electronic case report form;
EOS = end of study;
ET = early termination;
FACIT-Fatigue = Functional Assessment of Chronic Illness Therapy-Fatigue Scale;
LDH = lactate dehydrogenase;
PD = pharmacodynamics;
PK = pharmacokinetics;
PNH = paroxysmal nocturnal hemoglobinuria;
q4w = once every 4 weeks;
RBC = red blood cell

[a]Extension Period begins at the start of Day 183 dosing.
[b]Granulocyte and RBC clone size measured by high-sensitivity flow cytometry.
[c]Height at Days 575 and 911 only. Weight is collected pre-dose.
[d]Pregnancy testing is required only for female patients of childbearing potential (i.e., have achieved menarche). Serum pregnancy test is performed at early termination (ET) only, unless required by site policy. Urine pregnancy test at all other required time points. A negative pregnancy test result is required prior to administering study drug to female patients of childbearing potential at the indicated study visits.
[e]Investigator or designee assessment of the following events: fatigue, hemoglobinuria, abdominal pain, dyspnea, dysphagia, chest pain, and erectile dysfunction. On dosing days, assessments are performed prior to dosing.
[f]On dosing days, assessments are performed prior to dosing. Pediatric FACIT-Fatigue only in patients ≥5 years of age (self-reported by patients who were ≥8 years of age at the time of enrollment and reported by caregivers for patients who were ≥5 to <8 years of age at the time of enrollment).
[g]Abbreviated physical examination consists of a body system relevant examination based upon Investigator (or qualified designee) judgment and patient symptoms. At least one body system is checked for an abbreviated exam.
[h]Vital sign measurements are taken after the patient has been resting for at least 5 minutes and include systolic and diastolic BP (millimeters of mercury [mmHg]), heart rate (beats/minute), respiratory rate (breaths/minute), and temperature (degrees Celsius [C.] or degrees Fahrenheit [° F.]). On dosing days, vital signs are taken pre-dose.
[i]Single 12-lead ECG is collected at Day 911 or ET. Patients are supine for approximately 5 to 10 minutes before ECG collection and remain supine (but awake) during ECG collection.
[j]Clinical laboratory measurements are collected pre-dose and not from a heparinized line.
[k]Serum samples for PK/PD analyses are collected at end-of-infusion on Day 183. Pre-dose (within 0.5 hours prior to the start of infusion) and at end of infusion (within 0.5 hours after the end of infusion) on Days 351, 575, and 743; and at any time on Day 911 or early termination. To minimize needle sticks to the patient, the pre-dose sample is drawn through the venous access created for the dose infusion, prior to administration of the dose. End-of-infusion samples are drawn from the patient's opposite, non-infused arm. All collection times are recorded. In the event that supplemental dose is administered, pre-dose and end of infusion blood samples will be collected for PK/PD analysis. In the event of breakthrough hemolysis, a serum sample for PK/PD analysis is collected.
[l]Samples for ADA are collected pre-dose or at any time during the visit when a dose of a study drug is not administered.
[m]Review the Clinical Trial Participant Safety Information Card with the patient and discuss the importance of carrying the safety card at all times, and the risks ravulizumab treatment, including the risk of meningococcal infection.
[n]If a suspected event of breakthrough hemolysis occurs, LDH, PK and PD parameters are analyzed at the central laboratory. If the suspected event of breakthrough does not occur at a scheduled visit, an unscheduled visit occurs for evaluation of the patient and collection of the required LDH, PK and PD parameters.
[o]Dose regimen is based on body weight obtained at the study visit. If the study drug is prepared the night prior to the visit, the weight from the previous visit is used.
[p]Should a patient's weight change from <20 kg to ≥20 kg on a "q4w only" visit, the patient receives the q4w dose that day. At the patient's next q8w visit, the new q8w dose is given.

Abbreviations: ADA=antidrug antibody; ECG=electrocardiogram; eCRF=electronic case report form; EOS=end of study; ET=early termination; FACIT-Fatigue=Functional Assessment of Chronic Illness Therapy-Fatigue Scale; LDH=lactate dehydrogenase; PD=pharmacodynamics; PK=pharmacokinetics; PNH=paroxysmal nocturnal hemoglobinuria; q4w=once every 4 weeks; RBC=red blood cell

[a] Extension Period begins at the start of Day 183 dosing.
[b] Granulocyte and RBC clone size measured by high-sensitivity flow cytometry.
[c] Height at Days 575 and 911 only. Weight is collected pre-dose.
[d] Pregnancy testing is required only for female patients of childbearing potential (i.e., have achieved menarche). Serum pregnancy test is performed at early termination (ET) only, unless required by site policy. Urine pregnancy test at all other required time points. A negative pregnancy test result is required prior to administering study drug to female patients of childbearing potential at the indicated study visits.

$^e$ Investigator or designee assessment of the following events: fatigue, hemoglobinuria, abdominal pain, dyspnea, dysphagia, chest pain, and erectile dysfunction. On dosing days, assessments are performed prior to dosing.

$^f$ On dosing days, assessments are performed prior to dosing. Pediatric FACIT-Fatigue only in patients ≥5 years of age (self-reported by patients who were ≥8 years of age at the time of enrollment and reported by caregivers for patients who were ≥5 to <8 years of age at the time of enrollment).

$^g$ Abbreviated physical examination consists of a body system relevant examination based upon Investigator (or qualified designee) judgment and patient symptoms. At least one body system is checked for an abbreviated exam.

$^h$ Vital sign measurements are taken after the patient has been resting for at least 5 minutes and include systolic and diastolic BP (millimeters of mercury [mmHg]), heart rate (beats/minute), respiratory rate (breaths/minute), and temperature (degrees Celsius [C] or degrees Fahrenheit [° F.]). On dosing days, vital signs are taken pre-dose.

$^i$ Single 12-lead ECG is collected at Day 911 or ET. Patients are supine for approximately 5 to 10 minutes before ECG collection and remain supine (but awake) during ECG collection.

$^j$ Clinical laboratory measurements are collected pre-dose and not from a heparinized line.

$^k$ Serum samples for PK/PD analyses are collected at end-of-infusion on Day 183. Pre-dose (within 0.5 hours prior to the start of infusion) and at end-of-infusion (within 0.5 hours after the end of infusion) on Days 351, 575, and 743; and at any time on Day 911 or early termination. To minimize needle sticks to the patient, the pre-dose sample is drawn through the venous access created for the dose infusion, prior to administration of the dose. End-of-infusion samples are drawn from the patient's opposite, non-infused arm. All collection times are recorded. In the event that supplemental dose is administered, pre-dose and end of infusion blood samples will be collected for PK/PD analysis. In the event of breakthrough hemolysis, a serum sample for PK/PD analysis is collected.

$^l$ Samples for ADA are collected pre-dose or at any time during the visit when a dose of a study drug is not administered.

$^m$ Review the Clinical Trial Participant Safety Information Card with the patient and discuss the importance of carrying the safety card at all times, and the risks ravulizumab treatment, including the risk of meningococcal infection.

$^n$ If a suspected event of breakthrough hemolysis occurs, LDH, PK and PD parameters are analyzed at the central laboratory. If the suspected event of breakthrough does not occur at a scheduled visit, an unscheduled visit occurs for evaluation of the patient and collection of the required LDH, PK and PD parameters.

$^o$ Dose regimen is based on body weight obtained at the study visit. If the study drug is prepared the night prior to the visit, the weight from the previous visit is used.

$^p$ Should a patient's weight change from <20 kg to ≥20 kg on a "q4w only" visit, the patient receives the q4w dose that day. At the patient's next q8w visit, the new q8w dose is given.

5. Study Population

Pediatric patients (age <18 years) with a documented diagnosis of PNH are enrolled and treated with ravulizumab at approximately 40 investigative sites globally. Approximately 12 patients are enrolled to ensure at least 10 evaluable patients complete the 26-week period. Individuals who do not meet the criteria for participation in this study (screen failure) can be rescreened once.

Patients are eligible for enrollment in the study only if they meet all of the following criteria and none of the exclusion criteria:

1. Male and female patients <18 years of age and weighing ≥5 kg at the time of consent.
2. Documented diagnosis of PNH, confirmed by high-sensitivity flow cytometry evaluation (Borowitz, M. et al., *Cytometry B Clin. Cytom.*, 78:211-30, 2010) of red blood cells (RBCs) and white blood cells (WBCs), with granulocyte or monocyte clone size of ≥5%.
3. For patients not currently treated with eculizumab, presence of one or more of the following PNH-related signs or symptoms within three months of Screening: fatigue, hemoglobinuria, abdominal pain, shortness of breath (dyspnea), anemia, history of a major adverse vascular event (including thrombosis), dysphagia, or erectile dysfunction; or history of packed red blood cell (pRBC) transfusion due to PNH.
4. LDH values at Screening as follows:
   a. For patients not currently treated with eculizumab, LDH level ≥1.5×ULN.
   b. For patients who are currently taking eculizumab, LDH ≤1.5×ULN (sample must be obtained on a scheduled eculizumab-dosing day prior to dose administration [i.e., at trough eculizumab level] and analyzed by the central laboratory).
5. To reduce the risk of meningococcal infection (*N. meningitidis*), all patients must be vaccinated against meningococcal infections within three years prior to, or at the time of, initiating study drug. Patients who initiate study drug treatment less than two weeks after receiving a meningococcal vaccine receive treatment with appropriate prophylactic antibiotics until two weeks after vaccination. Patients who cannot be vaccinated receive antibiotic prophylaxis for the entire treatment period and for eight months following last dose.
6. Patients must have been vaccinated against *Haemophilus influenzae* type b (Hib) and *Streptococcus pneumoniae* according to national and local vaccination schedule guidelines, as appropriate.
7. Female patients of childbearing potential (i.e., have achieved menarche) and male patients with female partners of childbearing potential follow protocol-specified guidance for avoiding pregnancy while on treatment and for 8 months after last dose of study drug. Patient's legal guardian gives written informed consent and the patient gives written informed assent and comply with the study visit schedule.

Patients are excluded from study enrollment if they meet any of the following criteria:

1. Platelet count <30,000/mm³ (30×10⁹/L) at Screening.
2. Absolute neutrophil count <500/μL (0.5×10⁹/L) at Screening.
3. History of bone marrow transplantation.
4. History of *N. meningitidis* infection.
5. History of unexplained, recurrent infection.
6. Active systemic bacterial, viral, or fungal infection within 14 days prior to study drug administration on Day 1.
7. History of malignancy within 5 years of Screening with the exception of adequately treated nonmelanoma skin cancer or carcinoma in situ of the cervix.
8. History of or ongoing major cardiac, pulmonary, renal, endocrine, or hepatic disease (e.g., active hepatitis) that, in the opinion of the Investigator or Sponsor, precludes the patient's participation in an investigational clinical trial.
9. Unstable medical conditions (e.g., myocardial ischemia, active gastrointestinal bleed, severe congestive heart failure, anticipated need for major surgery within 6 months of Screening, coexisting chronic anemia unrelated to PNH) that makes them unlikely to tolerate the requirements of the protocol.
10. Concomitant use of anticoagulants is prohibited if not on a stable regimen for at least 2 weeks prior to Day 1.
11. History of hypersensitivity to any ingredient contained in the study drug, including hypersensitivity to murine proteins.
12. Females who plan to become pregnant or are currently pregnant or breastfeeding.
13. Females of childbearing potential who have a positive pregnancy test result at Screening or on Day 1.

14. Participation in another interventional treatment study or use of any experimental therapy within 30 days before initiation of study drug on Day 1 in this study or within 5 half-lives of that investigational product, whichever is greater.
15. Known or suspected history of drug or alcohol abuse or dependence within 1 year prior to the start of Screening.
16. Known medical or psychological condition(s) or risk factor that, in the opinion of the Investigator or Sponsor, might interfere with the patient's full participation in the study, pose any additional risk for the patient, or confound the assessment of the patient or outcome of the study.

6. Study Treatment

Ravulizumab is a humanized, anti-C5 mAb produced in Chinese hamster cells. The ravulizumab drug product is supplied for clinical studies as a sterile, preservative-free 10 mg/mL solution in single-use vials and is designed for infusion by diluting into commercially available saline (0.9% sodium chloride injection; country-specific pharmacopeia) for administration via IV infusion (see Table 3).

TABLE 3

| Study Drug | |
|---|---|
| Product Name | ravulizumab |
| Dosage Form | Concentrated solution (10 mg/mL) for infusion |
| Route of Administration | Intravenous infusion |
| Physical Description | Clear to translucent, slight whitish color, practically free from particles |
| Manufacturer | Alexion Pharmaceuticals, Inc. or Contracted Manufacturing Organization |

Ravulizumab is packaged in US Pharmacopeia/European Pharmacopeia Type 1 borosilicate glass vials and stoppered with a butyl rubber stopper with an aluminum overseal and a flip-off cap. Study drug is supplied in kits.

Upon arrival of the study drug kits at the study site, the pharmacist or designee promptly removes the study drug kits from the shipping cooler and stores them in their original cartons under refrigerated conditions at 2 C to 8 C (35° F. to 47° F.) and protected from light. Ravulizumab is not frozen. Study drug is stored in a secure, limited-access storage area, and the temperature is monitored daily.

The admixed drug product is at room temperature prior to administration. The material is not heated (e.g., by using a microwave or other heat source) other than by ambient air temperature.

Ravulizumab is not administered as an intravenous (IV) push or bolus injection. Infusions of study drug are prepared using aseptic technique. The patient's required dose of ravulizumab is further diluted into commercially available saline (0.9% sodium chloride; country-specific pharmacopeia) at the volume specified in Table 4. Ravulizumab admixture is administered to the patient using an IV tubing administration set via an infusion pump. Use of a 0.2 micron filter is required during infusion of ravulizumab.

TABLE 4

Dosing Reference Chart for Ravulizumab Dose Preparation

| Dose Type | Body Weight (kg)[a] | Dose (mg) | ravulizumab Volume (mL) | Saline Volume (mL) | Total Volume (mL) | Minimum Infusion Duration minutes (hours) | Maximum Infusion Rate (mL/hour) |
|---|---|---|---|---|---|---|---|
| Loading | ≥5 to <10 | 600 | 60 | 60 | 120 | 228 (3.8) | 31.5 |
| | ≥10 to <20 | 600 | 60 | 60 | 120 | 113 (1.9) | 63.1 |
| | ≥20 to <30 | 900 | 90 | 90 | 180 | 86 (1.5) | 120.0 |
| | ≥30 to <40 | 1200 | 120 | 120 | 240 | 77 (1.3) | 184.6 |
| | ≥40 to <60 | 2400 | 240 | 240 | 480 | 114 (1.9) | 253 |
| | ≥60 to <100 | 2700 | 270 | 270 | 540 | 102 (1.7) | 318 |
| | ≥100 | 3000 | 300 | 300 | 600 | 108 (1.8) | 333 |
| Maintenance | ≥5 to <10 | 300 | 30 | 30 | 60 | 113 (1.9) | 31.5 |
| | ≥10 to <20 | 600 | 60 | 60 | 120 | 113 (1.9) | 63.1 |
| | ≥20 to <30 | 2100 | 210 | 210 | 420 | 194 (3.3) | 127.2 |
| | ≥30 to <40 | 2700 | 270 | 270 | 540 | 167 (2.8) | 192.8 |
| | ≥40 to <60 | 3000 | 300 | 300 | 600 | 140 (2.4) | 250 |
| | ≥60 to <100 | 3300 | 330 | 330 | 660 | 120 (2.0) | 330 |
| | ≥100 | 3600 | 360 | 360 | 720 | 132 (2.2) | 328 |

[a]Body weight is obtained at the study visit. If the study drug is prepared the night prior to the visit, the weight from the previous visit is used.

Doses of study drug are only prepared and dispensed by qualified study personnel. Study drug is dispensed only to enrolled patients who are confirmed eligible for participation. Once study drug is prepared for a patient, it is only administered to that patient. Vials of study drug are for one-time use only and any drug product remaining in the vial is not used for another patient. Any drug remaining in the infusion tubing or infusion bag is not used for another patient.

[a] Body weight is obtained at the study visit. If the study drug is prepared the night prior to the visit, the weight from the previous visit is used.

Patients receive a loading dose of ravulizumab on Day 1, followed by maintenance dosing of ravulizumab on Day 15 and once every eight weeks (q8w) thereafter for patients weighing ≥20 kg, or once every four weeks (q4w) for patients weighing <20 kg, as shown in Table 5. With the agreement of the Medical Monitor, the 600 mg loading dose can be given to patients weighing ≥5 to <10 kg as two separate infusions administered no more than 24 hours apart. In addition, administration of a supplemental dose of ravulizumab is permitted. Dosages are based on the patient's body weight recorded on the day of dosing or the most recently recorded weight. For patients entering the study on eculizumab therapy, Day 1 of study treatment occurs 2 weeks from the patient's last dose of eculizumab.

TABLE 5

Loading and Maintenance Treatment Regimens

| Body Weight Range (kg)[a] | Loading Dose (mg) | Maintenance Doses (mg) | Maintenance Dosing Frequency |
|---|---|---|---|
| ≥5 to <10 | 600[b] | 300 | q4w |
| ≥10 to <20 | 600 | 600 | q4w |
| ≥20 to <30 | 900 | 2100 | q8w |
| ≥30 to <40 | 1200 | 2700 | q8w |
| ≥40 to <60 | 2400 | 3000 | q8w |
| ≥60 to <100 | 2700 | 3300 | q8w |
| ≥100 | 3000 | 3600 | q8w |

Abbreviations: q4w = once every 4 weeks; q8w = once every 8 weeks
[a]Dose regimen is based on body weight obtained at the study visit. If the study drug is prepared the night prior to the visit, the weight from the previous visit is used.
[b]The 600 mg loading dose can be given to patients weighing ≥5 to <10 kg as two separate infusions administered no more than 24 hours apart.

After the Primary Evaluation Period, all patients roll over into an Extension Period and continue their weight-based maintenance dose of ravulizumab on Day 183 and once every eight weeks (q8w) thereafter for patients weighing ≥20 kg, or once every four weeks (q4w) for patients weighing <20 kg, until the product is registered or approved (in accordance with country specific regulation) or for up to 2 years, whichever occurs first.

The actual time of all dose administrations, including any supplemental dose or dose administered as two separate infusions, is recorded. Due to its mechanism of action, the use of ravulizumab increases the patient's susceptibility to meningococcal infection (N. meningitidis). To reduce the risk of meningococcal infection, all patients are vaccinated against meningococcal infections within three years prior to, or at the time of, initiating study drug. Patients who initiate study drug treatment less than two weeks after receiving a meningococcal vaccine receive treatment with appropriate prophylactic antibiotics until two weeks after vaccination. Vaccines against serotypes A, C, Y, W135 and B, where available, are recommended to prevent common pathogenic meningococcal serotypes. Patients are vaccinated or revaccinated according to current national vaccination guidelines or local practice for vaccination use with eculizumab. Vaccination may not be sufficient to prevent meningococcal infection. Consideration is given per official guidance and local practice on the appropriate use of antibacterial agents and vaccination. All patients are monitored for early signs of meningococcal infection, evaluated immediately if infection is suspected, and treated with appropriate antibiotics, if necessary. Patients are also vaccinated against Hib and S. pneumoniae according to national and local vaccination schedule guidelines.

7. Efficacy Assessments

Administration of a packed red blood cell (pRBC) transfusion, including the hemoglobin result and symptoms that triggered the transfusion, and the number of units transfused, are documented in the electronic case report form (eCRF).

Blood and urine samples are collected at the times indicated in the Schedule of Assessments.

The following disease-related laboratory parameters are measured during the study: LDH, free hemoglobin, occult blood, urine, total C5, haptoglobin, reticulocyte count, PNH RBC clone size evaluated by high-sensitivity flow cytometry, and estimated glomerular filtration rate (calculated using the Schwartz formula).

The Investigator or designee record for each patient the presence or absence of the following signs and symptoms of PNH: fatigue, chest pain, hemoglobinuria, abdominal pain, dyspnea, dysphagia, erectile dysfunction, and red/dark urine or hemoglobinuria.

The Pediatric FACIT-Fatigue scale is a 13-item questionnaire that assesses fatigue and its impact upon daily activities and function over the preceding 7 days. Each item is scored on a 5-point scale, and total scores range from 0 to 52, with higher score indicating better QoL. The questionnaire is self-reported by patients who were ≥8 years of age at the time of enrollment and reported by caregivers for patients who were ≥5 to <8 years of age at the time of enrollment. Patients <5 years of age are assessed. The Pediatric FACIT-Fatigue Scale is shown in Table 6.

TABLE 6

Pediatric FACIT-Fatigue Scale

| | None of the time | A little bit of the time | Some of the time | Most of the time | All of the time |
|---|---|---|---|---|---|
| I feel tired... | 0 | 1 | 2 | 3 | 4 |
| I have energy (or strength)... | 0 | 1 | 2 | 3 | 4 |
| I could do my usual things at home... | 0 | 1 | 2 | 3 | 4 |
| I had trouble starting things because I was too tired... | 0 | 1 | 2 | 3 | 4 |
| I had trouble finishing things because I was too tired... | 0 | 1 | 2 | 3 | 4 |
| I needed to sleep during the day... | 0 | 1 | 2 | 3 | 4 |
| I got upset by being too tired to do the things I want to do... | 0 | 1 | 2 | 3 | 4 |
| Being tired made it hard for me to play or go out with my friends as much as I'd like... | 0 | 1 | 2 | 3 | 4 |
| I needed help doing my usual things at home... | 0 | 1 | 2 | 3 | 4 |
| I feel weak... | 0 | 1 | 2 | 3 | 4 |
| I was too tired to eat... | 0 | 1 | 2 | 3 | 4 |
| Being tired made me sad... | 0 | 1 | 2 | 3 | 4 |
| Being tired made me mad (angry)... | 0 | 1 | 2 | 3 | 4 |

Major adverse vascular events (MAVEs) are assessed as part of the planned evaluation for adverse events (AEs). The description of the MAVE, including the method of diagnosis (e.g., magnetic resonance imaging, ultrasound, angiogram), date of diagnosis, and date resolved (or ongoing) is collected on the eCRF as part of the patient's medical history (prior to baseline). A MAVE is defined as follows: thrombophlebitis/ deep vein thrombosis, pulmonary embolus, myocardial infarction, transient ischemic attack, unstable angina, renal vein thrombosis, acute peripheral vascular occlusion, mesenteric/visceral vein thrombosis or infarction, mesenteric/visceral arterial thrombosis or infarction, hepatic/portal vein thrombosis (Budd-Chiari syndrome), cerebral arterial occlusion/cerebrovascular accident, cerebral venous occlusion, renal arterial thrombosis, gangrene (non-traumatic; non-diabetic), amputation (non-traumatic; non-diabetic), and dermal thrombosis.

8. Safety Assessments

A review of demographic parameters, including age, gender, race and ethnicity is performed. A complete medical history is taken and documented. Weight and height are recorded. Head circumference is recorded for patients who are ≤3 years of age. The patient's PNH medical history, including PNH symptoms, date of diagnosis, PNH clone size, pRBC transfusions and history of any MAVEs, are documented at the Screening visit.

The patient's medical history, including prior and concomitant conditions/disorders and transfusion history, is recorded at the Screening Visit. Medication (prescription or over the counter, including vitamins and/or herbal supplements) use within 28 days prior to the start of Screening is also be recorded. Details of prior treatment with eculizumab, including dose level and frequency, are collected. Meningococcal vaccination within 3 years prior to the first dose of study drug, and vaccination history for Hib and *S. pneumoniae* from birth, is also recorded.

A physical examination includes the following assessments: general appearance; skin; head, ear, eye, nose, and throat; neck; lymph nodes; chest; heart; abdominal cavity; limb; central nervous system; and musculoskeletal system. An abbreviated physical examination consists of a body system relevant examination based upon Investigator judgment and patient symptoms. Physical growth (height, weight and head circumference [the latter only in patients ≤3 years of age]) is assessed.

Vital sign measurements are taken after the patient has been resting for at least five minutes, and include systolic and diastolic blood pressure (BP; millimeters of mercury [mmHg]), heart rate (beats/minute), respiratory rate (breaths/minute), and temperature (degrees Celsius [C] or degrees Fahrenheit [° F.]).

Samples for serum pregnancy, hematology, chemistry, coagulation, and urinalysis are performed at the times specified in the Schedule of Assessments. Specific laboratory assessments are provided in Table 7. Samples for laboratory assessments are collected before each study drug administration. An alternative blood sampling schedule for infants, for whom less blood volume is collected, must be used. If a suspected event of breakthrough hemolysis occurs, an unscheduled visit takes place at which a sample is collected for analysis of LDH and PK/PD by the central laboratory.

TABLE 7

| Laboratory Assessments | |
|---|---|
| Hematology | Clinical Chemistry |
| Free hemoglobin | Alanine aminotransferase |
| Haptoglobin | Albumin |
| Hematocrit | Alkaline phosphatase |
| Hemoglobin | Aspartate aminotransferase |
| Mean corpuscular hemoglobin | Bicarbonate |
| Platelet count | Blood urea nitrogen |

TABLE 7-continued

| Laboratory Assessments | |
|---|---|
| RBC count | Calcium |
| RBC distribution width | Chloride |
| RBC mean corpuscular volume | Creatinine |
| Reticulocyte count | Gamma-glutamyltransferase |
| WBC count | Glucose |
| WBC differential | Lactate dehydrogenase |
| Coagulation Panel | Magnesium |
| International normalized ratio | Phosphorus |
| Partial thromboplastin time | Potassium |
| Prothrombin time | Sodium |
| Urinalysis | Total bilirubin (direct and indirect) |
| Appearance | Total protein |
| Bilirubin | Uric acid |
| Blood | Other |
| Color | Antidrug antibody |
| Glucose | Beta human chorionic gonadotropin |
| Ketone | (females of childbearing potential only) |
| Nitrite | Chicken RBC assay |
| pH | Free and total C5 |
| Specific gravity | Pharmacokinetic assay |
| Urobilinogen | PNH clone size |
| Urine Chemistry | |
| Microalbumin | |

Abbreviations: C5=complement component 5; PNH=paroxysmal nocturnal hemoglobinuria; RBC=red blood cell; WBC=white blood cell It is anticipated that some laboratory values may be outside the normal value range due to the underlying disease. The Investigators should use their medical judgment when assessing the clinical significance of these values. Clinical significance is defined as any variation in laboratory measurements that has medical relevance and that results in a change in medical care. If clinically significant laboratory changes from baseline value are noted, the changes are documented as adverse events. The Investigator also assesses the relationship to study treatment for all clinically significant out-of-range values. The Investigator monitors the patient through additional laboratory assessments until (1) values have returned to the normal range or baseline level, or (2) in the judgment of the Investigator, values that are outside the normal range are not related to the administration of study drug or other protocol-specific procedures.

For females of childbearing potential (i.e., have achieved menarche), a serum or urine pregnancy test (beta-human chorionic gonadotropin [β-hCG]) is performed according to the Schedule of Assessments.

Blood samples are analyzed for the hematology parameters listed in Table 7. Blood samples are also analyzed for the serum chemistry parameters listed in Table 7. Indirect bilirubin is calculated from total and direct bilirubin values. Therefore, indirect bilirubin results are not available if direct bilirubin is below the limit of quantification.

Chemistry assessments are performed at the time points specified in the Schedule of Assessments. The estimated glomerular filtration rate is calculated using the Schwartz formula for all visits at which serum chemistries are collected. Blood samples are also analyzed for the coagulation parameters listed in Table 7.

Urine samples are analyzed for the parameters listed in Table 7. A microscopic examination of urine samples is performed if the results of the macroscopic analysis are abnormal.

For each patient, single 12-lead digital electrocardiograms (ECGs) are collected according to the Schedule of Assessments. Patients are supine for approximately 5 to 10 minutes before ECG collection and remain supine (but awake) during ECG collection. The ECG is assessed to see whether it is within normal limits and to determine the clinical significance of the results.

Blood samples are collected to test for presence and titer of antidrug antibodies to ravulizumab in serum prior to study drug administration as indicated in the Schedule of Assessments. Further characterization of antibody responses is conducted as appropriate, including binding and neutralizing antibodies, PK/PD, safety and activity of ravulizumab.

An adverse event is any untoward medical occurrence in a patient administered a pharmaceutical product that does not necessarily have a causal relationship with this treatment. An adverse event can therefore, be any unfavorable or unintended sign (e.g., an abnormal laboratory finding), symptom, or disease temporally associated with the use of a medicinal product, whether or not considered related to the medicinal product.

Situations in which an untoward medical occurrence did not occur (e.g., hospitalization for elective surgery if planned before the start of the study, admissions for social reasons or for convenience), and anticipated day-to-day fluctuations of pre-existing disease(s) or condition(s) present or detected at the start of the study that do not worsen are not adverse events. Transfusions are treated as efficacy endpoints. Transfusions administered in the inpatient or outpatient setting should not be captured as adverse events or serious adverse events unless identified as such. Lack of drug effect is not an adverse event in clinical studies, because the purpose of the clinical study is to establish drug effect.

A medication error (including intentional misuse, abuse, and overdose of the product) or use other than what is defined in the protocol is not considered an adverse event unless there is an untoward medical occurrence as a result of a medication error.

Cases of pregnancy that occur during maternal or paternal exposure to investigational product are to be reported within 24 hours of Investigator/site awareness. Data on fetal outcome and breastfeeding is collected for regulatory reporting and safety evaluation.

The severity of adverse events is graded using Common Terminology Criteria for Adverse Events (CTCAE) version 4.03 or higher. A grading (severity) scale is provided for each adverse event term. Each CTCAE term is a Lowest Level Term (LLT) per the Medical Dictionary for Regulatory Activities (MedDRA®). Each LLT is coded to a MedDRA preferred term (PT). Grade refers to the severity of the adverse event. The CTCAE assigns a grade of 1 through 5, with unique clinical descriptions of severity for each adverse event, as set forth in Table 8.

TABLE 8

Adverse Event Severity Grading Scale

| Grade | Description |
|---|---|
| Grade 1 | Mild; asymptomatic or mild symptoms; clinical or diagnostic observations only; intervention not indicated |
| Grade 2 | Moderate; minimal, local or noninvasive intervention indicated; limiting age-appropriate instrumental ADL[a] |
| Grade 3 | Severe or medically significant, but not immediately life-threatening; hospitalization or prolongation of hospitalization indicated; disabling; limiting self-care ADL[b] |
| Grade 4 | Life-threatening consequences; urgent intervention indicated. |
| Grade 5 | Death related to AE. |

Abbreviations: ADL = activities of daily living; AE = adverse event

[a]Instrumental ADL refers to preparing meals, shopping for groceries or clothes, using the telephone, managing money, etc.
[b]Self-care ADL refers to bathing, dressing and undressing, feeding self, using the toilet, taking medications, and not bedridden.

Severity and seriousness are differentiated. Severity describes the intensity of an adverse event, while the term seriousness refers to an adverse event that has met specific criteria for a serious adverse event. A causality assessment (Unrelated, Unlikely, Possible, Probable, or Definite) is provided for all adverse events (both serious and nonserious) based upon the Investigator's medical judgment and the observed symptoms associated with the event, as set forth in Table 9.

TABLE 9

Causality Assessment Descriptions

| Assessment | Description |
|---|---|
| Not Related/Unrelated | Suggests that there is no causal association between the investigational product and the reported event. |
| Unlikely Related | Suggests that the clinical picture is highly consistent with a cause other than the investigational product but attribution cannot be made with absolute certainty and a relationship between the investigational product and AE cannot be excluded with complete confidence. |
| Possibly Related | Suggests that treatment with the investigational product may have caused or contributed to the AE (i.e., the event follows a reasonable temporal sequence from the time of drug administration and/or follows a known response pattern to the investigational product, but could also have been produced by other factors). |
| Probably Related | Suggests that a reasonable temporal sequence of the event with the investigational product administration exists and the likely causal association of the event with the investigational product. This is be based upon the known pharmacological action of the investigational product, known or previously reported adverse reactions to the investigational product or class of drugs, or judgment based on the Investigator's clinical experience. |
| Definitely Related | Temporal relationship to the investigational product, other conditions (concurrent illness, concurrent medication reaction, or progression/expression of disease state) do not appear to explain event, corresponds with the known pharmaceutical profile, improvement on discontinuation, reappearance on rechallenge. |

A SAE is any untoward medical occurrence that: results in death, is life-threatening (i.e., patient was at risk of death at the time of the event), requires inpatient hospitalization or prolongation of existing hospitalization, results in persistent or significant disability/incapacity, or is a congenital anomaly/birth defect.

Important medical events that may not result in death, be immediately life-threatening, or require hospitalization are considered a serious adverse event when, based upon appropriate medical judgment, they jeopardize the patient or require intervention to prevent one of the outcomes listed above.

Suspected unexpected serious adverse reactions (SUSARs) are serious events that are not listed in the Investigator's Brochure and that the Investigator identifies as related to investigational product or procedure.

All adverse events are collected from the signing of the informed consent form (ICF) until 56 days after the last dose of study drug for patients with ET or until 56 days after the last dose of study drug for patients who complete the study. All adverse events are recorded on the eCRF upon becoming aware of their occurrence. Investigators are instructed to report the serious adverse event, including their assessment (e.g., severity, seriousness, and potential relatedness to study drug).

9. Pharmacokinetics (PK) and Pharmacodynamics (PD)

Blood samples for determination of serum drug concentrations and PD assessments are collected before and after administration of study drug at the time points indicated in the Schedule of Assessments. The actual date and time (24-hour clock time) of each sampling is recorded. In the event of breakthrough hemolysis, an additional PK/PD sample is required.

End of infusion blood samples for PK and PD assessment is collected from the arm opposite to the arm used for infusing drug. Assessments for PK/PD are as follows: serum ravulizumab concentration over time, free and total C5 concentrations over time, and cRBC hemolytic activity over time 10. Statistical Methods and Planned Analyses A clinical study report (CSR) is produced based on efficacy, safety, PK, PD and immunogenicity data collected through the end of the 26-week Primary Evaluation Period (Day 183). A final CSR to summarize long-term efficacy, safety, PK, PD and immunogenicity parameters is produced at study completion.

This study is descriptive in nature and not statistically powered for hypothesis testing due to the rarity of disease in pediatric patients. Approximately 12 patients are enrolled to ensure at least 10 evaluable patients complete the 26-week period. A sample size of 10 is expected to be sufficient to adequately describe PK/PD in pediatric patients with PNH. Efficacy analyses are performed on the Full Analysis Set (FAS). The FAS includes all patients who received at least one dose of ravulizumab and have at least one post-baseline assessment.

Safety analyses are performed on the Safety Set, defined as all patients who receive at least one dose of ravulizumab.

Pharmacokinetic and PD analyses are performed on all patients who receive at least one dose of ravulizumab and who have evaluable PK and PD data.

Patient demographic and baseline characteristics, including medical history and transfusion history, are summarized for the clinical study report (FAS) and Safety sets. All patients are included in the summaries of patient disposition, which describe the frequency and percentage of patients screened and treated and who completed or withdraw from the study, along with reason for withdrawal from the study.

The numbers of patients who are treated, discontinue treatment (along with reason for treatment discontinuation), complete or withdraw from the Primary Evaluation Period (along with reason for withdrawal), enter the Extension Period, and complete or withdraw from the Extension Period (along with reason for withdrawal) are tabulated.

Each patient's prior and concomitant medication use is coded using the World Health Organization Drug Dictionary, and the frequency and percentage of concomitant medications is summarized. Medications are summarized by Anatomic-Therapeutic-Chemical class and generic name using frequency counts and percentages of patients in the Safety set. The number of infusions received per patient is tabulated for the FAS and Safety sets. Efficacy analyses is performed using the FAS. Continuous variables are summarized using descriptive statistics, including number of observations and mean, SD, median, minimum and maximum values. Categorical variables are summarized by frequency counts and percentage of patients. Analyses are conducted separately for naïve and previously eculizumab-treated patients.

The following definitions are used for adverse events. A pretreatment adverse event is any adverse event that starts after providing informed consent, but before the first infusion of study drug. A treatment-emergent adverse event is any adverse event that starts during or after the first infusion of study drug. A treatment-emergent serious adverse event is a treatment-emergent AE (TEAE) that is serious.

The incidence of TEAEs, TEAEs leading to withdrawal from the study, TEAEs leading to study treatment discontinuation, drug-related TEAEs, TEAEs during study drug administration, severe TEAEs and SAEs are summarized. All adverse events are coded using MedDRA version 18 or higher, and summarized by system organ class and preferred term. Detailed by-patient listings of TEAEs, SAEs, related TEAEs, TEAEs during study drug administration, TEAEs leading to withdrawal from the study and TEAEs leading to study treatment discontinuation are provided.

Adverse changes from baseline in physical examination findings are classified as adverse events and analyzed accordingly.

Vital signs are summarized descriptively at baseline and postbaseline time points and for changes from baseline by treatment group.

Height, weight and head circumference (the latter only for patients <3 years of age) are summarized descriptively at baseline and post-baseline time points and for changes from baseline by treatment group.

Changes in clinical chemistry, hematology, and urinalysis results from baseline to post-baseline study time points are summarized descriptively. Shift tables over time are presented for all central laboratory values, where applicable, using normal, low or high based on normal range values. Listings of patients with abnormal results are provided. By-patient data listings of ECG parameters are provided. Changes from baseline in electrocardiogram intervals (PR, RR, QT and QTcF) are provided. QT interval is corrected for heart rate using Fridericia's formula (QTcF).

Incidence and titers for antidrug antibodies (ADAs) to ravulizumab are summarized in tabular format. Individual serum concentration data for all patients who receive at least one dose of ravulizumab and who have evaluable PK data are used to derive PK parameters for ravulizumab.

Graphs of mean serum concentration-time profiles are constructed. Graphs of serum concentration-time profiles for individual patients are also provided. Actual dose administration and sampling times is used for all calculations. Descriptive statistics are calculated for serum concentration data at each sampling time, as appropriate. Assessment of population-PK is considered using data from this study or in combination with data from other studies.

PD analyses are performed for all patients who receive at least one dose of ravulizumab and who have evaluable PD data.

Descriptive statistics are presented for all ravulizumab PD endpoints at each sampling time. The PD effects of ravulizumab administered IV are evaluated by assessing the absolute values and changes and percentage changes from baseline in total and free C5 serum concentrations and change from baseline in cRBC hemolysis over time, as appropriate.

Assessments of ravulizumab PK/PD relationships are explored using data from this study or in combination with data from other studies. Analyses are conducted separately for naïve and previously eculizumab-treated patients.

If a Day 1 assessment is missing, the Screening assessment is used as the baseline assessment.

| SEQUENCE SUMMARY |
| --- |

SEQ ID NO: 1
GYIFSNYWIQ

SEQ ID NO: 2
EILPGSGSTEYTENFKD

SEQ ID NO: 3
YFFGSSPNWYFDV

SEQ ID NO: 4
GASENIYGALN

SEQ ID NO: 5
GATNLAD

SEQ ID NO : 6
QNVLNTPLT

SEQ ID NO: 7
QVQLVQSGAE VKKPGASVKV SCKASGYIFS NYWIQWVRQA PGQGLEWMGE
ILPGSGSTEY TENFKDRVTM TRDISTSTVY MELSSLRSED TAVYYCARYF
FGSSPNWYFD VWGQGTLVTV SS

SEQ ID NO: 8
DIQMTQSPSS LSASVGDRVT ITCGASENIY GALNWYQQKP GKAPKLLIYG
ATNLADGVPS RFSGSGSGTD FTLTISSLQP EDFATYYCQN VLNTPLTFGQ
GTKVEIK

SEQ ID NO: 9
ASTKGPSVFP LAPCSRSTSE STAALGCLVK DYFPEPVTVS WNSGALISGV
HTFPAVLQSS GLYSLSSVVT VPSSNFGTQT YTCNVDHKPS NTKVDKTVER
KCCVECPPCP APPVAGPSVF LFPPKPKDTL MISRTPEVTC VVVDVSQEDP
EVQFNWYVDG VEVHNAKTKP REEQFNSTYR VVSVLIVLHQ DWINGKEYKC
KVSNKGLPSS IEKTISKAKG QPREPQVYTL PPSQEEMTKN QVSLTCLVKG
FYPSDIAVEW ESNGQPENNY KTTPPVLDSD GSFFLYSRLT VDKSRWQEGN
VFSCSVMHEA LHNHYTQKSL SLSLGK

SEQ ID NO: 10
QVQLVQSGAE VKKPGASVKV SCKASGYIFS NYWIQWVRQA PGQGLEWMGE
ILPGSGSTEY TENFKDRVTM TRDISTSTVY MELSSLRSED TAVYYCARYF
FGSSPNWYFD VWGQGTLVTV SSASTKGPSV FPLAPCSRST SESTAALGCL
VKDYFPEPVT VSWNSGALTS GVHTFPAVLQ SSGLYSLSSV VTVPSSNFGT
QTYTCNVDHK PSNTKVDKTV ERKCCVECPP CPAPPVAGPS VFLFPPKPKD
TLMISRTPEV TCVVVDVSQE DPEVQFNWYV DGVEVHNAKT KPREEQFNST
YRVVSVLTVL HQDWINGKEY KCKVSNKGLP SSIEKTISKA KGQPREPQVY

SEQUENCE SUMMARY

TLPPSQEEMT NQVSLTCLVK GFYPSDIAVE WESNGQPENN YKITPPVLDS

DGSFFLYSRL TVDKSRWQEG NVFSCSVMHE ALHNHYTQKS LSLSLGK

SEQ ID NO: 11

DIQMTQSPSS LSASVGDRVT ITCGASENIY GALNWYQQKP GKAPKLLIYG

ATNLADGVPS RFSGSGSGTD FTLTISSLQP EDFATYYCQN VLNTPLTFGQ

GTKVEIKRTV AAPSVFIFPP SDEQLKSGTA SVVCLLNNFY PREAKVQWKV

DNALQSGNSQ ESVTEQDSKD STYSLSSTLT LSKADYEKHK VYACEVTHQG

LSSPVTKSEN RGEC

SEQ ID NO: 12

QVQLVQSGAE VKKPGASVKV SCKASGHIFS NYWIQWVRQA PGQGLEWMGE

ILPGSGHTEY TENFKDRVTM TRDTSTSTVY MELSSLRSED TAVYYCARYF

FGSSPNWYFD VWGQGTLVTV SS

SEQ ID NO: 13

ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APPVAGPSVF LFPPKPKDTL MISRTPEVTC VVVDVSQEDP

EVQFNWYVDG VEVHNAKTKP REEQFNSTYR VVSVLIVLHQ DWLNGKEYKC

KVSNKGLPSS IEKTISKAKG QPREPQVYTL PPSQEEMTKN QVSLTCLVKG

FYPSDIAVEW ESNGQPENNY KTTPPVLDSD GSFFLYSRLT VDKSRWQEGN

VFSCSVLHEA LHSHYTQKSL SLSLGK

SEQ ID NO: 14

QVQLVQSGAE VKKPGASVKV SCKASGHIFS NYWIQWVRQA PGQGLEWMGE

ILPGSGHTEY TENFKDRVTM TRDISTSTVY MELSSLRSED TAVYYCARYF

FGSSPNWYFD VWGQGTLVTV SSASTKGPSV FPLAPCSRST SESTAALGCL

VKDYFPEPVT VSWNSGALTS GVHTFPAVLQ SSGLYSLSSV VTVPSSNFGT

QTYTCNVDHK PSNTKVDKTV ERKCCVECPP CPAPPVAGPS VFLFPPKPKD

TLMISRTPEV TCVVVDVSQE DPEVQFNWYV DGVEVHNAKT KPREEQFNST

YRVVSVLIVL HQDWLNGKEY KCKVSNKGLP SSIEKTISKA KGQPREPQVY

TLPPSQEEMT KNQVSLTCLV KGFYPSDIAV EWESNGQPEN NYKTTPPVLD

SDGSFFLYSR LTVDKSRWQE GNVFSCSVLH EALHSHYTQK SLSLSLGK

SEQ ID NO: 15

ASTKGPSVFP LAPCSRSTSE STAALGCLVK DYFPEPVTVS WNSGALTSGV

HTFPAVLQSS GLYSLSSVVT VISSNFGTQT YTCNVDHKPS NTKVDKTVER

KCCVECPPCP APPVAGPSVF LFPPKPKDTL YITREPEVTC VVVDVSHEDP

EVQFNWYVDG MEVHNAKTKP REEQFNSTER VVSVLTVVHQ DWLNGKEYKC

KVSNKGLPAP IEKTISKTKG QPREPQVYTL PPSREEMTKN QVSLTCLVKG

FYPSDIAVEW ESNGQPENNY KTTPPMLDSD GSFFLYSKLT VDKSRWQQGN

VFSCSVMHEA LHNHYTQKSL SLSPGK

SEQ ID NO: 16

QVQLVQSGAE VKKPGASVKV SCKASGYIFS NYWIQWVRQA PGQGLEWMGE

ILPGSGSTEY TENFKDRVTM TRDISTSTVY MELSSLRSED TAVYYCARYF

| SEQUENCE SUMMARY |
|---|
| FGSSPNWYFD VWGQGTLVTV SSASTKGPSV FPLAPCSRST SESTAALGCL |
| VKDYFPEPVT VSWNSGALTS GVHTFPAVLQ SSGLYSLSSV VTVTSSNFGT |
| QTYTCNVDHK PSNTKVDKTV ERKCCVECPP CPAPPVAGPS VFLFPPKPKD |
| TLYITREPEV TCVVVDVSHE DPEVQFNWYV DGMEVHNAKT KPREEQENST |
| FRVVSVLIVV HQDWLNGKEY KCKVSNKGLP APIEKTISKT KGQPREPQVY |
| TLPPSREEMT KNQVSLTCLV KGFYPSDIAV EWESNGQPEN NYKTTPPMLD |
| SDGSFFLYSK LTVDKSRWQQ GNVFSCSVMH EALHNHYTQK SLSLSPGK |
| SEQ ID NO: 17 |
| GASENIYHALN |
| SEQ ID NO: 18 |
| EILPGSGHTEYTENFKD |
| SEQ ID NO: 19 |
| GHIFSNYWIQ |
| SEQ ID NO: 20 |
| QVQLVQSGAE VKKPGASVKV SCKASGHIFS NYWIQWVRQA PGQGLEWMGE |
| ILPGSGHTEY TENFKDRVTM TRDTSTSTVY MELSSLRSED TAVYYCARYF |
| FGSSPNWYFD VWGQGTLVTV SSASTKGPSV FPLAPCSRST SESTAALGCL |
| VKDYFPEPVT VSWNSGALTS GVHTFPAVLQ SSGLYSLSSV VTVPSSNFGT |
| QTYTCNVDHK PSNTKVDKTV ERKCCVECPP CPAPPVAGPS VFLFPPKPKD |
| TLMISRTPEV TCVVVDVSQE DPEVQFNWYV DGVEVHNAKT KPREEQFNST |
| YRVVSVLTVL HQDWINGKEY KCKVSNKGLP SSIEKTISKA KGQPREPQVY |
| TLPPSQEEMT KNQVSLTCLV KGFYPSDIAV EWESNGQPEN NYKTTPPVLD |
| SDGSFFLYSR LTVDKSRWQE GNVFSCSVMH EALHNHYTQK SLSLSLGK |
| SEQ ID NO: 21 |
| SYAIS |
| SEQ ID NO: 22 |
| GIGPFFGTANYAQKFQG |
| SEQ ID NO: 23 |
| DTPYFDY |
| SEQ ID NO: 24 |
| SGDSIPNYYVY |
| SEQ ID NO: 25 |
| DDSNRPS |
| SEQ ID NO: 26 |
| QSFDSSLNAEV |
| SEQ ID NO: 27 |
| QVQLVQSGAE VKKPGSSVKV SCKASGGTFS SYAISVWRQA PGQGLEWMGG |
| IGPFFGTANY AQKFQGRVTI TADESTSTAY MELSSLRSED TAVYYCARDT |
| PYFDYWGQGT LVTVSS |
| SEQ ID NO: 28 |
| DIELTQPPSV SVAPGQTARI SCSGDSIPNY YVYWYQQKPG QAPVLVIYDD |
| SNRPSGIPER FSGSNSGNTA TLTISGTQAE DEADYYCQSF DSSLNAEVEG |
| GGTKLTVL |
| SEQ ID NO: 29 |
| NYIS |

SEQUENCE SUMMARY

IIDPDDSYTEYSP SFQG
SEQ ID NO: 30

YEYGGFDI
SEQ ID NO: 31

SGDNIGNSYVH
SEQ ID NO: 32

KDNDRPS
SEQ ID NO: 33

GTYDIESYV
SEQ ID NO: 34

EVQLVQSGAE VKKPGESLKI SCKGSGYSFT NYISWVRQMP GKGLEWMGII DPDDSYTEYS PSFQGQVTIS ADKSISTAYL QWSSLKASDT AMYYCARYEY GGFDIWGQGT LVTVSS
SEQ ID NO: 35

SYELTQPPSV SVAPGQTARI SCSGDNIGNS YVHWYQQKPG QAPVLVIYKD NDRPSGIPER FSGSNSGNTA TLTISGTQAE DEADYYCGTY DIESYVFGGG TKLTVL
SEQ ID NO: 36

SSYYVA
SEQ ID NO: 37

AIYTGSGATYKASWAKG
SEQ ID NO: 38

DGGYDYPTHAMHY
SEQ ID NO: 39

QASQNIGSSLA
SEQ ID NO: 40

GASKTHS
SEQ ID NO: 41

QSTKVGSSYGNH
SEQ ID NO: 42

QVQLVESGGG LVQPGGSLRL SCAASGETSH SSYYVAWVRQ APGKGLEWVG AIYTGSGATY KASWAKGRFT ISKDISKNQV VLTMINMDPV DTATYYCASD GGYDYPTHAM HYWGQGTLVT VSS
SEQ ID NO: 43

DVVMTQSPSS LSASVGDRVT ITCQASQNIG SSLAWYQQKP GQAPRLLIYG ASKTHSGVPS RFSGSGSGTD FTLTISSLQP EDVATYYCQS TKVGSSYGNH FGGGTKVEIK
SEQ ID NO: 44

QVQLVESGGG LVQPGRSLRL SCAASGFTVH SSYYMAWVRQ APGKGLEWVG AIFTGSGAEY KAEWAKGRVT ISKDISKNQV VLTMINMDPV DTATYYCASD AGYDYPTHAM HYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEL RRGPKVELFP PKPKDTLMIS RTPEVTCVVV DVSHEDPEVK FNWYVDGVEV HNAKIKPREE QYNSTYRVVS VLTVLHQDWL NGKEYKCKVS NKGLPSSIEK TISKAKGQPR EPQVYTLPPS REEMTKNQVS LTCLVKGFYP SDIAVEWESN GQPENNYKTT
SEQ ID NO: 45

SEQUENCE SUMMARY

PPVLDSDGSF FLYSKLTVDK SRWQQGNVFS CSVLHEALHA HYTRKELSLS

P

SEQ ID NO: 46

DIQMTQSPSS LSASVGDRVT ITCRASQGIS SSLAWYQQKP GKAPKLLIYG

ASETESGVPS RFSGSGSGTD FTLTISSLQP EDFATYYCQN TKVGSSYGNT

FGGGTKVEIK RTVAAPSVFI FPPSDEQLKS GTASVVCLLN NFYPREAKVQ

WKVDNALQSG NSQESVTEQD SKDSTYSLSS TLILSKADYE KHKVYACEVT

HQGLSSPVTK SFNRGEC

What is claimed is:

1. A method of treating a human pediatric patient with Paroxysmal Nocturnal Hemoglobinuria (PNH), the method comprising administering to the patient an effective amount of an anti-C5 antibody comprising heavy and light chains comprising the amino acid sequences shown in SEQ ID NOs:14 and 11, respectively, wherein the anti-C5 antibody is administered intravenously:

(a) once on Day 1 at a dose of 600 mg to a patient weighing ≥5 to <10 kg, 600 mg to a patient weighing ≥10 to <20 kg, 900 mg to a patient weighing ≥20 to <30 kg, or 1200 mg to a patient weighing ≥30 to <40 kg; and (b) on Day 15 and every four weeks thereafter at a dose of 300 mg to a patient weighing ≥5 to <10 kg or 600 mg to a patient weighing ≥10 to <20 kg; or on Day 15 and every eight weeks thereafter at a dose of 2100 mg to a patient weighing ≥20 to <30 kg, or 2700 mg to a patient weighing ≥30 to <40 kg.

2. The method of claim 1, wherein the anti-C5 antibody binds to human C5 at pH 7.4 and 25 C with an affinity dissociation constant ($K_D$) that is in the range 0.1 nM≤$K_D$≤1 nM.

3. The method of claim 1, wherein the anti-C5 antibody binds to human C5 at pH 6.0 and 25 C with a $K_D$≥10 nM.

4. The method of claim 1, wherein the anti-C5 antibody is administered to a patient weighing ≥5 to <10 kg:
   (a) once on Day 1 at a dose of 600 mg; and
   (b) on Day 15 and every four weeks thereafter at a dose of 300 mg.

5. The method of claim 1, wherein the anti-C5 antibody is administered to a patient weighing ≥10 to <20 kg:
   (a) once on Day 1 at a dose of 600 mg; and
   (b) on Day 15 and every four weeks thereafter at a dose of 600 mg.

6. The method of claim 1, wherein the anti-C5 antibody is administered to a patient weighing ≥20 to <30 kg:
   (a) once on Day 1 at a dose of 900 mg; and
   (b) on Day 15 and every eight weeks thereafter at a dose of 2100 mg.

7. The method of claim 1, wherein the anti-C5 antibody is administered to a patient weighing ≥30 to <40 kg:
   (a) once on Day 1 at a dose of 1200 mg; and
   (b) on Day 15 and every eight weeks thereafter at a dose of 2700 mg.

8. The method of claim 1, further comprising measuring a serum trough concentration of the anti-C5 antibody to maintain a serum trough concentration of the anti-C5 antibody of 100 μg/mL or greater in the patient.

9. The method of claim 1, wherein the method comprises an administration cycle comprising a total of 26 weeks of treatment.

10. The method of claim 1, further comprising determining that the treated patient has:
   (a) terminal complement inhibition;
   (b) a reduction of hemolysis as assessed by lactate dehydrogenase (LDH) levels compared to baseline;
   (c) produces at least one therapeutic effect selected from the group consisting of: a reduction or cessation in abdominal pain, dyspnea, dysphagia, chest pain and erectile dysfunction compared to baseline;
   (d) a shift toward normal levels of at least one hemolysis related hematologic biomarker selected from the group consisting of: free hemoglobin, haptoglobin, reticulocyte count, PNH red blood cell (RBC) clone and D dimer;
   (e) a reduction in the need for blood transfusions compared to baseline;
   (f) a reduction in major adverse vascular events (MAVEs);
   (g) a shift toward normal levels of estimated glomerular filtration rate (eGFR) or spot urine:albumin:creatinine and plasma brain natriuretic peptide (BNP); and/or
   (h) a change from baseline in quality of life, assessed via the Functional Assessment of Chronic Illness Therapy (FACIT) Fatigue Scale, version 4 and the European Organisation for Research and Treatment of Cancer, Quality of Life Questionnaire Core 30 Scale compared to baseline.

11. The method of claim 1, wherein the patient has previously been treated with eculizumab and Day 1 of the treatment is two weeks or more from the patient's last dose of eculizumab.

12. The method of claim 1, wherein the anti-C5 antibody is ravulizumab.

* * * * *

SEQUENCE LISTING

<160> NUMBER OF SEQ ID NOS: 46

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Glu Ile Leu Pro Gly Ser Gly Ser Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Tyr Phe Phe Gly Ser Ser Pro Asn Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Asn Val Leu Asn Thr Pro Leu Thr
1               5

<210> SEQ ID NO 7
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly Ser Thr Glu Tyr Thr Glu Asn Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 8
```

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105

```
<210> SEQ ID NO 9
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

```
Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
                275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 10
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
```

```
                225                 230                 235                 240

Val Phe Leu Phe Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 11
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly His Thr Glu Tyr Thr Glu Asn Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser
            115                 120

<210> SEQ ID NO 13
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

```
Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
                180                 185                 190

Leu Asn Gly Lys Glu Tyr Lys Cys Lys Val Ser Asn Lys Gly Leu Pro
                195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
            290                 295                 300

Ser Val Leu His Glu Ala Leu His Ser His Tyr Thr Gln Lys Ser Leu
305                 310                 315                 320

Ser Leu Ser Leu Gly Lys
            325

<210> SEQ ID NO 14
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly His Thr Glu Tyr Thr Glu Asn Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
```

Gly Gln Gly Thr Leu Val Thr Val Ser Ser Ala Ser Thr Lys Gly Pro
            100                 105                 110

Ser Val Phe Pro Leu Ala Pro Cys Ser Arg Ser Thr Ser Glu Ser Thr
        115                 120                 125

Ala Ala Leu Gly Cys Leu Val Lys Asp Tyr Phe Pro Glu Pro Val Thr
        130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
            165                 170                 175

Val Pro Ser Ser Asn Phe Gly Thr Gln Thr Tyr Thr Cys Asn Val Asp
        180                 185                 190

His Lys Pro Ser Asn Thr Lys Val Asp Lys Thr Val Glu Arg Lys Cys
        195                 200                 205

Cys Val Glu Cys Pro Pro Cys Pro Ala Pro Pro Val Ala Gly Pro Ser
        210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser Gln Glu Asp Pro
            245                 250                 255

Glu Val Gln Phe Asn Trp Tyr Val Asp Gly Val Glu Val His Asn Ala
        260                 265                 270

Lys Thr Lys Pro Arg Glu Glu Gln Phe Asn Ser Thr Tyr Arg Val Val
        275                 280                 285

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Leu His Glu Ala
        420                 425                 430

Leu His Ser His Tyr Thr Gln Lys Ser Leu Ser Leu Ser Leu Gly Lys
        435                 440                 445

<210> SEQ ID NO 15
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Ser Thr Lys Gly Pro Ser Val Phe Pro Leu Ala Pro Cys Ser Arg
1               5                   10                  15

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Tyr Ile Thr Arg Glu Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 16
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Ser Asn Tyr
            20                  25                  30
```

-continued

```
Trp Ile Gln Trp Val Arg Gln Ala Pro Gly Gln Gly Leu Glu Trp Met
             35                  40                  45
Gly Glu Ile Leu Pro Gly Ser Gly Ser Thr Glu Tyr Thr Glu Asn Phe
 50                  55                  60
Lys Asp Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Tyr Phe Phe Gly Ser Ser Pro Asn Trp Tyr Phe Asp Val Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Thr Ser Ser Asn Phe Gly Thr Gln Thr Tyr Thr Cys Asn Val Asp
        195                 200                 205
His Lys Pro Ser Asn Thr Lys Val Asp Lys Thr Val Glu Arg Lys Cys
    210                 215                 220
Cys Val Glu Cys Pro Pro Cys Pro Ala Pro Pro Val Ala Gly Pro Ser
225                 230                 235                 240
Val Phe Leu Phe Pro Pro Lys Pro Lys Asp Thr Leu Tyr Ile Thr Arg
                245                 250                 255
Glu Pro Glu Val Thr Cys Val Val Val Asp Val Ser His Glu Asp Pro
            260                 265                 270
Glu Val Gln Phe Asn Trp Tyr Val Asp Gly Met Glu Val His Asn Ala
        275                 280                 285
Lys Thr Lys Pro Arg Glu Glu Gln Phe Asn Ser Thr Phe Arg Val Val
    290                 295                 300
Ser Val Leu Thr Val Val His Gln Asp Trp Leu Asn Gly Lys Glu Tyr
305                 310                 315                 320
Lys Cys Lys Val Ser Asn Lys Gly Leu Pro Ala Pro Ile Glu Lys Thr
                325                 330                 335
Ile Ser Lys Thr Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

```
<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Ala Ser Glu Asn Ile Tyr His Ala Leu Asn
1               5                   10

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Glu Ile Leu Pro Gly Ser Gly His Thr Glu Tyr Thr Glu Asn Phe Lys
1               5                   10                  15

Asp

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly His Ile Phe Ser Asn Tyr Trp Ile Gln
1               5                   10

<210> SEQ ID NO 20
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly His Thr Glu Tyr Thr Glu Asn Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
                100                 105                 110
```

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 21

Ser Tyr Ala Ile Ser
1               5

```
<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Ile Gly Pro Phe Phe Gly Thr Ala Asn Tyr Ala Gln Lys Phe Gln
1               5                   10                  15

Gly

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Thr Pro Tyr Phe Asp Tyr
1               5

<210> SEQ ID NO 24
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Gly Asp Ser Ile Pro Asn Tyr Tyr Val Tyr
1               5                   10

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Asp Ser Asn Arg Pro Ser
1               5

<210> SEQ ID NO 26
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gln Ser Phe Asp Ser Ser Leu Asn Ala Glu Val
1               5                   10

<210> SEQ ID NO 27
<211> LENGTH: 116
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Val Trp Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser
        115

<210> SEQ ID NO 28
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
            100                 105

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asn Tyr Ile Ser
```

```
<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Ile Asp Pro Asp Asp Ser Tyr Thr Glu Tyr Ser Pro Ser Phe Gln
1               5                   10                  15

Gly

<210> SEQ ID NO 31
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Glu Tyr Gly Gly Phe Asp Ile
1               5

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ser Gly Asp Asn Ile Gly Asn Ser Tyr Val His
1               5                   10

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Lys Asp Asn Asp Arg Pro Ser
1               5

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Thr Tyr Asp Ile Glu Ser Tyr Val
1               5
```

```
<210> SEQ ID NO 35
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
            115

<210> SEQ ID NO 36
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu
            100                 105

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 37

Ser Ser Tyr Tyr Val Ala
1               5

<210> SEQ ID NO 38
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Ile Tyr Thr Gly Ser Gly Ala Thr Tyr Lys Ala Ser Trp Ala Lys
1               5                   10                  15

Gly

<210> SEQ ID NO 39
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Asp Gly Gly Tyr Asp Tyr Pro Thr His Ala Met His Tyr
1               5                   10

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gln Ala Ser Gln Asn Ile Gly Ser Ser Leu Ala
1               5                   10

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Ala Ser Lys Thr His Ser
1               5

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42
```

```
Gln Ser Thr Lys Val Gly Ser Tyr Gly Asn His
1               5                   10
```

<210> SEQ ID NO 43
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser His Ser Ser
                20                  25                  30

Tyr Tyr Val Ala Trp Val Arg Gln Ala Pro Gly Lys Gly Leu Glu Trp
            35                  40                  45

Val Gly Ala Ile Tyr Thr Gly Ser Gly Ala Thr Tyr Lys Ala Ser Trp
        50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Gly Gly Tyr Asp Tyr Pro Thr His Ala Met His Tyr
            100                 105                 110

Trp Gly Gln Gly Thr Leu Val Thr Val Ser Ser
        115                 120
```

<210> SEQ ID NO 44
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

```
Asp Val Val Met Thr Gln Ser Pro Ser Ser Leu Ser Ala Ser Val Gly
1               5                   10                  15

Asp Arg Val Thr Ile Thr Cys Gln Ala Ser Gln Asn Ile Gly Ser Ser
                20                  25                  30

Leu Ala Trp Tyr Gln Gln Lys Pro Gly Gln Ala Pro Arg Leu Leu Ile
            35                  40                  45

Tyr Gly Ala Ser Lys Thr His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Thr Lys Val Gly Ser Ser
                85                  90                  95

Tyr Gly Asn His Phe Gly Gly Gly Thr Lys Val Glu Ile Lys
            100                 105                 110
```

<210> SEQ ID NO 45
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Leu His Glu Ala Leu His Ala His Tyr Thr Arg Lys Glu Leu Ser
        435                 440                 445

Leu Ser Pro
    450

<210> SEQ ID NO 46
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```